United States Patent
Wei et al.

(10) Patent No.: US 12,098,395 B2
(45) Date of Patent: *Sep. 24, 2024

(54) POLYPEPTIDE WITH FUNCTION OF TARGETING RECOGNITION OF IMMUNE CELLS AND APPLICATION THEREOF

(71) Applicant: Keyangle Life Technology Co., Ltd., Guangdong (CN)

(72) Inventors: Yuan'an Wei, Guangdong (CN); Xueshu Liu, Guangdong (CN)

(73) Assignee: KEYANGLE LIFE TECHNOLOGY CO., LTD., Guangdong (CN)

( * ) Notice: Subject to any disclaimer, the term of this patent is extended or adjusted under 35 U.S.C. 154(b) by 721 days.

This patent is subject to a terminal disclaimer.

(21) Appl. No.: 17/255,308

(22) PCT Filed: Jul. 19, 2019

(86) PCT No.: PCT/CN2019/096707
§ 371 (c)(1),
(2) Date: May 25, 2021

(87) PCT Pub. No.: WO2020/048244
PCT Pub. Date: Mar. 12, 2020

(65) Prior Publication Data
US 2022/0002686 A1    Jan. 6, 2022

(30) Foreign Application Priority Data
Sep. 7, 2018 (CN) .......................... 201811049702.3

(51) Int. Cl.
| | | |
|---|---|---|
| *C12N 9/12* | (2006.01) | |
| *A61K 49/00* | (2006.01) | |
| *G01N 21/64* | (2006.01) | |
| *G01N 21/76* | (2006.01) | |
| *G01N 33/569* | (2006.01) | |

(52) U.S. Cl.
CPC ........ *C12N 9/1205* (2013.01); *A61K 49/0056* (2013.01); *C12Y 207/01028* (2013.01); *G01N 21/6428* (2013.01); *G01N 21/6458* (2013.01); *G01N 21/76* (2013.01); *G01N 33/56966* (2013.01); *G01N 2021/6439* (2013.01); *G01N 2333/91215* (2013.01)

(58) Field of Classification Search
CPC ............ A61K 49/0041; A61K 49/0056; C12N 9/1205; C12N 9/88; C12Y 207/01028; C12Y 406/01015; G01N 2021/6439; G01N 21/6428; G01N 21/6458; G01N 21/76; G01N 2333/91215; G01N 33/56966; G01N 33/56972
See application file for complete search history.

(56) References Cited

U.S. PATENT DOCUMENTS

2023/0176053 A1* 6/2023 Wei ................ C12Y 207/01028
435/7.24

OTHER PUBLICATIONS

Cabezas, et al., "Identification of human and rat FAD-AMP lyase (cyclic FMN forming) as ATP-dependent dihydroxyacetone kinases", Biochemical and Biophysical Research Communications 338 (2005) 1682-1689.
Cabezas, et al., UniProtKB/Swiss-Prot:Q3LXA3.2.
English translation of the International Search Report issued to PCT/CN2019/096707, date mailed Oct. 25, 2019.
English translation of Written Opinion of the International Searching Authority for PCT/CN2019/096707.

* cited by examiner

*Primary Examiner* — Galina M. Yakovleva
(74) *Attorney, Agent, or Firm* — Hoffmann & Baron, LLP

(57) ABSTRACT

The present disclosure relates to a polypeptide recognizing immune cells, the polypeptide includes the following amino acid sequences: (a) an amino acid sequence containing C-terminal fragment sequence EQPDPGAVAAAAIL-RAILE of human Triokinase/FMN cyclase and its homologous sequence; or (b) an amino acid sequence that is substantially identical to the amino acid sequence described in (a), the substantially identical means 70% or more sequence identity to the amino acid sequence described in (a). The present invention also relates to a nucleic acid sequence encoding the polypeptide; a polypeptide probe used for targeting recognition of immune cells and containing the polypeptide described above and a reporter; a kit containing the probe described above; and, related applications of the polypeptide or probe described above.

4 Claims, 13 Drawing Sheets
Specification includes a Sequence Listing.

i.                                  ii.                                 iii.

A.

B.

C.

D.

SEQUENCE LISTING

```
<160> NUMBER OF SEQ ID NOS: 11

<210> SEQ ID NO 1
<211> LENGTH: 19
<212> TYPE: PRT
<213> ORGANISM: Homo sapiens

<400> SEQUENCE: 1

Glu Gln Pro Asp Pro Gly Ala Val Ala Ala Ala Ala Ile Leu Arg Ala
1               5                   10                  15

Ile Leu Glu

<210> SEQ ID NO 2
<211> LENGTH: 20
<212> TYPE: PRT
<213> ORGANISM: Homo sapiens

<400> SEQUENCE: 2

Leu Glu Gln Pro Asp Pro Gly Ala Val Ala Ala Ala Ala Ile Leu Arg
1               5                   10                  15
```

Ala Ile Leu Glu
            20

<210> SEQ ID NO 3
<211> LENGTH: 23
<212> TYPE: PRT
<213> ORGANISM: Homo sapiens

<400> SEQUENCE: 3

Glu Gln Pro Asp Pro Gly Ala Val Ala Ala Ala Ile Leu Arg Ala
1               5                   10                  15

Ile Leu Glu Val Leu Gln Ser
            20

<210> SEQ ID NO 4
<211> LENGTH: 36
<212> TYPE: PRT
<213> ORGANISM: Homo sapiens

<400> SEQUENCE: 4

Lys Asn Met Glu Ala Gly Ala Gly Arg Ala Ser Tyr Ile Ser Ser Ala
1               5                   10                  15

Arg Leu Glu Gln Pro Asp Pro Gly Ala Val Ala Ala Ala Ile Leu
            20                  25                  30

Arg Ala Ile Leu
            35

<210> SEQ ID NO 5
<211> LENGTH: 42
<212> TYPE: PRT
<213> ORGANISM: Homo sapiens

<400> SEQUENCE: 5

Thr Lys Asn Met Glu Ala Gly Ala Gly Arg Ala Ser Tyr Ile Ser Ser
1               5                   10                  15

Ala Arg Leu Glu Gln Pro Asp Pro Gly Ala Val Ala Ala Ala Ala Ile
            20                  25                  30

Leu Arg Ala Ile Leu Glu Val Leu Gln Ser
            35                  40

<210> SEQ ID NO 6
<211> LENGTH: 23
<212> TYPE: PRT
<213> ORGANISM: Gallus gallus

<400> SEQUENCE: 6

Leu Gln Pro Asp Pro Gly Ala Val Ala Ala Ala Val Leu Arg Ala
1               5                   10                  15

Val Leu Glu Gly Leu Gln Gly
            20

<210> SEQ ID NO 7
<211> LENGTH: 26
<212> TYPE: PRT
<213> ORGANISM: Rattus norvegicus

<400> SEQUENCE: 7

Asp Gln Pro Asp Pro Gly Ala Val Ala Ala Ala Ile Phe Arg Ala
1               5                   10                  15

Ile Leu Glu Val Leu Gln Thr Lys Ala Ala
            20                  25

```
<210> SEQ ID NO 8
<211> LENGTH: 26
<212> TYPE: PRT
<213> ORGANISM: Canis lupus

<400> SEQUENCE: 8

Asp Gln Pro Asp Pro Gly Ala Val Ala Ala Ala Ala Ile Leu Arg Thr
1               5                   10                  15

Ile Leu Glu Val Leu Gln Ser Gln Gly Val
            20                  25

<210> SEQ ID NO 9
<211> LENGTH: 26
<212> TYPE: PRT
<213> ORGANISM: Sus scrofa

<400> SEQUENCE: 9

Asp Gln Pro Asp Pro Gly Ala Val Ala Ala Ala Ala Ile Leu Arg Ala
1               5                   10                  15

Ile Leu Glu Val Leu Gln Ser Gln Gly Ala
            20                  25

<210> SEQ ID NO 10
<211> LENGTH: 23
<212> TYPE: PRT
<213> ORGANISM: Macaca mulatta

<400> SEQUENCE: 10

Glu Gln Pro Asp Pro Gly Ala Val Ala Ala Ala Ile Leu Arg Ala
1               5                   10                  15

Ile Leu Glu Val Leu Gln Ser
            20

<210> SEQ ID NO 11
<211> LENGTH: 24
<212> TYPE: PRT
<213> ORGANISM: Artificial Sequence
<220> FEATURE:
<223> OTHER INFORMATION: Synthesized

<400> SEQUENCE: 11

Glu Gln Pro Asp Pro Gly Ala Val Ala Ala Ala Ile Leu Arg Ala
1               5                   10                  15

Ile Leu Glu Val Leu Gln Ser Lys
            20
```

POLYPEPTIDE WITH FUNCTION OF TARGETING RECOGNITION OF IMMUNE CELLS AND APPLICATION THEREOF

CROSS-REFERENCE TO RELATED APPLICATIONS

The present application is a National Stage Application claiming the priority of co-pending PCT Application No. PCT/CN2019/096707 filed Jul. 19, 2019, which claims priority from Chinese Patent Application No. 201811049702.3, filed Sep. 7, 2018. The priority applications are herein specifically incorporated by reference in their entirety.

INCORPORATION BY REFERENCE

The instant application contains a Sequence Listing encoded in text format which was filed electronically by EFS-web and is hereby incorporated by reference in its entirety. Said txt format Sequence Listing, created on May 21, 2024 named "2234-5 PCTUS Amended Sequence Listing.txt" and 3,668 bytes in size.

TECHNICAL FIELD

The present disclosure relates to the fields of molecular biology, as well as cell detection and imaging. In particular, the present disclosure relates to a type of polypeptides for targeting recognition of immune cells, to a probe or a kit containing the polypeptide, and to a method for immunolabeling.

BACKGROUND

Immune cells mediate immune responses within the body, and include many different types of cells. These cells circulate throughout the blood and lymphatic systems and can be recruited to damaged tissue and sites of infection. Different types of immune cells are classified according to their functions and morphology. Most of the immune cells originate from hematopoietic stem cells and follow different pathways to develop and differentiate by responding to internal and external signals of the cell. From the classic immunological view, it believes that the mononuclear phagocytic system is a bone marrow-derived myeloid cell population, in which monocytes circulate in blood, bone marrow, and spleen without steady proliferation, then it differentiates into macrophages after leave blood and enter tissues. Macrophages are inherent phagocytes in lymphatic and non-lymphatic tissues and are considered to involve in tissue homeostasis by eliminating apoptotic cells and producing growth factors. However, the phenotypes, homeostatic cycles, and functions of these cells in different tissues can show very obvious heterogeneity (Geissmann et al., Development of monocytes, macrophages and dendritic cells, Science. 2010 Feb. 5; 327(5966): 656-61). This type of cells play many different roles in normal tissue development, homeostasis, tissue repair, and immune response against pathogens. Mature monocytes/macrophages have high motility in vivo. In related tissues, after phagocytosing bacteria, pathogens and dead cells, monocytes/macrophages can enter lymph nodes or organs, such as spleen, through neighbouring lymph vessels, and present antigens to other lymphocytes, such as T or B cells.

It has been discovered in recent years that macrophages in many adult tissues originate from embryonic development stages, rather than from circulating monocytes. Many tissues have macrophages derived from embryo and circulating monocytes (also known as circulating macrophages or adult macrophages). These two types of macrophages form macrophage populations in adult tissues. This new understanding of macrophages within tissues has arisen a re-examination of the function of circulating monocytes. The inflammatory responses can trigger monocytes to differentiate into macrophages, however, it is unclear whether resident and newly recruited macrophages perform the same function during the inflammatory responses (Slava Epelman, Kory J. Lavine, and Gwendalyn J Randolph, Origin and Functions of Tissue Macrophages, *Immunity* 41, Jul. 17, 2014, 21-35). As a result, macrophages may be activated to transform to different subpopulations and express different surface markers in different anatomic sites, or even in the same anatomic site, due to different origins and different environmental stimulations produced by the tissue microenvironment. Thus, it would be difficult to use, or give contradictory results by use of single biomarker antibody to identify different subpopulations of macrophages. For example, in experiments using Kumming mice as the animal model, better results can be obtained by using F4/80, CD11c, and CD68 antibodies to identify peritoneal, alveolar, and abdominal wall macrophages, respectively.

On the other hand, due to the wide distribution and multi-functions, in vivo identification and imaging of a wide range of monocytes/macrophages, such as performing molecular imaging on abdominal cavity, respiratory tract, intestine, whole organs, muscle tissues, and the like, can provide intuitive and sensitive information at the cellular and molecular levels on the changes and the development of the immune system in an organism, in addition to the occurrence and development of inflammation and tumorigenesis. Undoubtedly, imaging of monocyte/macrophages populations is very important to obtain an accurate diagnosis of diseases. To achieve this, a broad-spectrum monocyte/macrophage recognition probe is needed.

Therefore, making use of targeted molecular imaging probe of monocytes/macrophages to perform imaging has broad industrial applications in many fields.

Currently, both in vivo and in vitro identification and imaging of monocytes/macrophages mostly use the corresponding antibodies to recognize various biomarkers or receptors of cells for identification and labeling. Based on this, a variety of histoimmunology and cellular immunology methods, which use primary antibodies in combination with secondary antibodies or use direct-labeled antibodies, has been developed. However because antibodies are macromolecular proteins, their preparation and production involve a series of complex steps. During the preparation and production processes, there are many factors that may affect the activities of antibodies, resulting in the fact that the quality of the antibodies is unstable, and has great fluctuations from batch to batch. There is no uniform standard for the quality of the same antibody sold by different manufacturers. In addition, when fluorescent staining and labeling of monocytes/macrophages are carried out in vivo, the antigen-antibody binding and labeling could encounter challenges such as short fluorescence maintenance time.

Compared to proteins or antibodies, polypeptides do not exhibit a strictly three-dimensional active structure as those of proteins, and have low immunogenicity. Polypeptides are easy to be obtained through chemical synthesis, and are able to endure relatively stringent chemical modification and labeling while maintaining their activities. In addition, polypeptides have high affinity, easier penetration through tissues, and faster plasma clearance rates. Better pharmacokinetic properties can be achieved through modification of peptide structures.

Molecular imaging emerged in the early 21st century, since then it has been widely used in life sciences, medical researches, drug development, and other fields because it was easy to use and gave direct and sensitive results. Currently, molecular imaging technology has been developed to include Optical Imaging (OI), Magnetic Resonance Imaging (MRI) and Radionuclide Imaging, and others, for example, Positron Emission Tomography (PET) and Single Photon Emission Computed Tomography (SPECT) and so on. However, each modality imaging method has its own advantages and disadvantages, and multi-modality imaging where multiple imaging technologies are jointly used will be the trend of future development. The in vivo molecular imaging technology of mammals allows researchers to directly monitor cell activity and molecular change behaviors within living organisms. However, the most important part for in vivo molecular imaging is the preparation of an appropriate in vivo targeting recognition probe.

Therefore, there is a need to provide a new targeted probe suitable for recognizing monocytes/macrophages for in vivo imaging or targeted drug delivery.

SUMMARY

One of the purposes of the present disclosure is to provide a novel functional polypeptide that can realize targeting recognition of immune cells, especially monocyte precursors and monocytes/macrophages.

Another purpose of the present disclosure is to provide a nucleic acid sequence encoding the polypeptide described above.

Yet another purpose of the present disclosure is to provide a probe containing the polypeptide described above for detecting monocyte precursors and monocytes/macrophages.

Yet another purpose of the present disclosure is to provide a kit containing the probe described above.

Yet another purpose of the present disclosure is to provide a method for immune-cell labeling using the probe described above.

Yet another purpose of the present disclosure is to provide use of the polypeptide or probe described above in preparation of a reagent for in vivo imaging.

In one aspect of the present disclosure, the polypeptide for targeting recognition of immune cells comprises: (a) an amino acid sequence containing the C-terminal fragment EQPDPGAVAAAAILRAILE (SEQ ID NO.:1) of human Triokinase/FMN cyclase; or (b) an amino acid sequence that is substantially identical to the amino acid sequence described in (a), wherein the term"substantially identical" refers to having 80% or more sequence identity to the amino acid sequence described in (a).

Further, the amino acid sequence described in (a) may be EQPDPGAVAAAAILRAILE (SEQ ID NO.:1), LEQPDPGAVAAAAILRAILE (SEQ ID NO.:2), EQPDPGAVAAAAILRAILEVLQS (SEQ ID NO.: 3), KNMEAGAGRASYISSARLEQPDPGAVAAAAILRAIL (SEQ IDNO.:4), or TKNMEAGAGRASYISSARLEQPDPGAVAAAAILRAILEVLQS (SEQ ID NO.:5).

Further, the amino acid sequence, of (b) which is substantially identical to the amino acid sequence defined above in (a), refers to an amino acid sequence obtained through modification, substitution or deletion of one or more amino acids in the amino acid sequence described above in (a). The specific method for the modification, substitution, or deletion may be any method known in the prior art.

Further, the amino acid sequence described in (b) is a sequence contained in a C-terminal fragment of a non-human Triokinase/FMN cyclase and has 80% or more sequence identity to the amino acid sequence described in (a).

Preferably, the amino acid sequence described in (b) has 81%, 82%, 83%, 84%, 85%, 86%, 87%, 88%, 89%, 90%, 91%, 92%, 93%, 94%, 95%, 96%, 97%, 98% or more than 99% sequence identity to the amino acid sequence described in (a).

More preferably, the amino acid sequence described in (b) may be LQPDPGAVAAAAVLRAVLEGLQG (SEQ ID NO.:6), DQPDPGAVAAAAIFRAILEVLQTKAA (SEQ ID NO.:7), DQPDPGAVAAAAILRTILEVLQSQGV (SEQ ID NO.:8), DQPDPGAVAAAAILRAILEVLQSQGA (SEQ ID NO.:9) or EQPDPGAVAAAAILRAILEVLQS (SEQ ID NO.:10).

Further, the immune cells described herein may comprise lymphocytes, dendritic cells, monocyte precursors, monocytes/macrophages, basophilic, eosinophilic, and mastocytes, preferably monocyte precursors and monocytes/macrophages.

As used herein, the term "Triokinase/FMN cyclase" means an enzyme which is capable of catalyzing the phosphorylation of dihydroxyacetone and glyceraldehydes, and cleavage of ribonucleosidediphosphate-X compounds (in which FAD is the optimal substrate), and can inhibit IFIH1-mediated cellular antiviral response (Negative regulation of MDA5—but not RIG-I-mediated innate antiviral signaling by the dihydroxyacetone kinase, Feici Diao et al., Proc Natl Acad Sci USA. 2007 Jul. 10; 104(28):11706-11). Triokinase/FMN cyclase (also known as DAK protein) was first discovered in prokaryotic/eukaryotic microorganisms (B. Emi et al. Small Substrate, Big Surprise:Fold, Function and Phylogeny of Dihydroxyacetone Kinases, *Cell. Mol. Life Sci.* 2006, 63:890-900), and was reported to be able to catalyze the phosphorylation of dihydroxyacetone to produce dihydroxyacetone phosphate (Dha-P). The FAD-AMP lyase (also known as FMN cyclase) was found in rat liver extracts in 2005 and has homologous amino acid sequences with those DAK proteins of microorganisms. It was further confirmed that DAK proteins have dual functions of kinases and cyclase.

In the Uniprot protein database, the latest name of the DAK proteins is Triokinase/FMN cyclase. The C-terminal fragment of Triokinase/FMN cyclase has been found to be highly conserved in animals, especially in mammals (including humans) (A. Cabezas et al., Identification of human and rat FAD-AMP lyase (cyclic FMN forming) as ATP-dependent dihydroxyacetone kinases, *Biochemical and Biophysical Research Communications*, 2005, 338: 1682-1689). As shown in FIG. 1A, the C-terminal fragments of the Triokinase/FMN cyclase is highly conserved among vanous animals, with high homology and similarity. In addition, it was found that the C-terminal fragments of the Triokinase/FMN cyclases in the Uniprot database have 100% sequence identity (see FIG. 1B) among from 20 mammal species (comprising primates such as humans, orangutans, and monkeys). The coding gene of the human Triokinase/FMN cyclase is located on chromosome 11, region 11q12.2, with GenBank accession number DQ138290, and geneID: 26007 (also numbered as DKFZP586B1621).

However, none of the prior reports and art discloses or implies that Triokinase/FMN cyclase can recognize immune cells, or monocyte precursors and monocytes/macrophages.

The present disclosure finds and verifies for the first time that a polypeptide containing a C-terminal fragment of Triokinase/FMN cyclase can specifically recognize immune cells, in particular, can specifically recognize monocyte precursors and monocytes/macrophages. This will greatly simplify the in vivo labeling or imaging process of monocyte precursors and monocytes/macrophages, and improve the imaging effect simultaneously.

In addition, according to some embodiments of the present disclosure, it was proved that a conserved amino acid sequence contained by the C-terminal fragments of the Triokinase/FMN cyclases in both humans and other animals (e.g., cows, dogs, and rats, etc.) has similar functions to the amino acid sequence of (a), i.e. can realize targeting recognition of immune cells, especially monocyte precursors and monocytes/macrophages.

In the present disclosure, there is no particular restriction on animal species, for example, birds and mammals. Examples of birds may comprise chickens, ducks, and other bird species; examples of mammals may comprise mice, rats, rabbits, pigs, dogs, cows, and primates.

It should be understood by those skilled in the art that the polypeptide in the present disclosure may be a polypeptide fragment from a natural protein, or be obtained by a well-known peptide synthesis method.

Further, the polypeptide according to the present disclosure may comprise 80 or less amino acid residues, preferably comprise 70, 60, 55, 50, 45, 44, 43, 42, 42, 41, 40 or less amino acid residues, more preferably, comprise 6 to 45 amino acid residues, and most preferably, comprise 8 to 41 amino acid residues. For example, the polypeptide according to the present disclosure may comprise 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41 amino acid residues.

Further, the polypeptide according to the present disclosure may comprise a fragment of 80 or less amino acid residues from the C-terminal fragments of human or non-human Triokinase/FMN cyclases, or site-directed modification-containing fragment thereof.

Further, the polypeptide of the present disclosure can specifically recognize immune cells, preferably specifically recognize monocyte precursors and monocytes/macrophages.

In another aspect of the present disclosure, a nucleic acid sequence encoding the polypeptide described above is provided.

In yet another aspect of the present disclosure, a probe for targeting recognition of immune cells is provided, the probe comprise of the polypeptide of the present disclosure described above and a reporter, wherein the reporter may be linked to the N- and/or C-terminal of the polypeptide.

The N- and/or C-terminal of the polypeptide of the present disclosure may be directly linked to a reporter. Alternatively, the C- or N-terminal of the polypeptide may be linked with one or more amino acid residues which have an easily modifiable side chain, and then further linked to a reporter. The amino acid residues which have an easily modifiable side chain may be, for example, cysteine (C) or lysine (K). It should be understood that there are no particular restriction to the linkage of the reporter with the polypeptide, and the reporter can be linked by any suitable method known in the prior art, preferably linked by covalent binding.

The reporter may be a chromogenic enzyme, a fluorescent labeling group, a chemiluminescent labeling group, an isotope, or a magnetic functional group.

The chromogenic enzyme can catalyze the conversion of a substrate into a colored compound, and may be, for example, peroxidase, alkaline phosphatase, and the like.

The fluorescent labeling group may be ones commonly used in the art and be a fluorescent group such as fluorescent protein, rhodamine, fluorescein, anthocyanin dye, cyanine dye (e.g., near-infrared cyanine dyes), AlexaFluor® dye, nanoparticles, and/or quantum dots, (Huang Zhiping et al., Application of polypeptide fluorescent probes in protein detection, *Chinese Science: Chemistry*, 2013, Volume 43, Issue 8: 1013-1021). For example, the fluorescent labeling group may be carboxyfluorescein (FAM), fluorescein thiocyanate (FITC), dansyl chloride, 2,4-dinitrobenzene, carboxyrhodamine 110, Texas Red®, pentamethine cyanine dye (Cys5®), heptamethine cyanine dyes (Cys7®), green fluorescent protein (GFP), enhanced green fluorescent protein (EGFP), red fluorescent protein (RFP), and the like.

Further, the magnetic functional group may be a group capable of magnetic resonance imaging, and changing relaxation efficiency, and preferably be a paramagnetic group, such as chelate of gadolinium or manganese, ultra-small paramagnetic or superparamagnetic, nanoparticles (e.g., iron oxide magnetic nanoparticles, specifically an imaging reporter for magnetic resonance imaging using iron trioxide or ferroferric oxide magnetic nanoparticles and the like).

Further, the isotope may be radionuclide, such as radionuclide used in positron emission tomography (PET and) single photon emission computed tomography (SPECT) and other imaging processes. For example, the isotope may be one or more selected from $^{11}C$, $^{13}N$, $^{15}O$, $^{18}F$, $^{75}Br$, $^{76}Br$, $^{32}P$, $^{35}S$, $^{122}I$, $^{124}I$, $^{62}Cu$ $^{64}Cu$ $^{68}Ga$, $^{86}Y$, $^{99m}Tc$, $^{123}I$, $^{125}I$, $^{111}In$, $^{201}Tl$ and the like.

Further, the probe can achieve targeting recognition of immune cells, more preferably monocyte precursors and monocytes/macrophages.

Further, the probe may be used for in vivo imaging in mammals. Preferably, the probe may be used for in vivo imaging, and more preferably, be used for targeted imaging of pulmonary macrophages.

In yet another aspect of the present disclosure, a kit containing the probe described above is provided. The probe may be in a liquid or solid form. The kit may further contain an initial solvent, a diluent, and operating instructions. The initial solvent may be DMSO, DMF, and the like. The diluent may be phosphate buffer, cell culture medium, and the like, for example, may be DMEM.

The kit is suitable for in vivo imaging of immune cells, preferably monocyte precursors and monocytes/macrophages. In addition, the kit also may be used for in vitro immunostaining and/or microscopic analysis of cells or tissues. For example, kit may be used for immunostaining or microscopic analysis of cultured cells, tissue sections, smears, and cell climbing slices.

In yet another aspect of the present disclosure, the present disclosure provides a method for in vivo imaging of mammals. The method uses an effective amount of the probe described above for in vivo imaging of mammals, for example, the probe is injected into a living body by the method commonly used in the art for in vitro imaging.

In yet another aspect of the present disclosure, the present disclosure provides an application of the polypeptide or probe described above in preparation of a kit for in vivo imaging of mammals is provided.

In yet another aspect of the present disclosure, the present disclosure provides an application of the polypeptide or probe described above in preparation of a reagent for in vivo imaging of immune cells.

In yet another aspect of the present disclosure, the present disclosure provides a composition containing the polypeptide described above as an active ingredient, for imaging of immune cells, preferably for in vivo or in vitro imaging monocyte precursors and monocytes/macrophages.

In yet another aspect of the present disclosure, the present disclosure provides a method of immune labeling, including the probes described above incubating with cells or tissues (such as tissue sections, smears, cell slides, or living tissues) to be labeled.

As used therein, the term "targeting recognition" means that the polypeptide of the present disclosure specifically interacts with some immune cells, such as monocyte precursors and monocytes/macrophages.

Compared with commonly used antibody or protein-based monocyte/macrophage recognition processes, the small molecular polypeptide of the present disclosure for targeting recognition of immune cells, such as macrophages, have many advantages.

Firstly, similar to the recognition of mouse macrophages by monoclonal antibodies against F4/80, the recognition of macrophages by the small molecule polypeptide of the present disclosure is not interfered by the Fc receptor specific to on the surface of immune cells (see F4/80, a monoclonal antibody directed specifically against the mouse marcrophage, Jonathan M. Austyn and Siamon Gordon, *Eur. J. Immunol.* 1981, 11: 805-815), and has no obvious tissue specificity, for example, it can recognize both abdominal macrophages and alveolar macrophages. Through the experiment of mouse primary tissue cell culture in vitro, the present disclosure shows that the polypeptide described above can selectively recognize monocyte precursors and abdominal macrophages, which are obtained from mouse femur bone marrow and cultured in vitro. The polypeptide of the present disclosure has no obvious response to the tissue-specific phenotype of macrophages, and has much weaker staining of somatic cells other than macrophages in the tissue. Therefore, the polypeptide of the present disclosure exhibits excellent selectivity on macrophages.

Secondly, in a strict sense, the small molecular polypeptide of the present disclosure has no tertiary structure as those of proteins. The polypeptide sequences of the present disclosure are derived from natural triokinase/FMN cyclases of animals, and thus have low immunogenicit. Labeling in a living body substantially does not trigger immunogenicity, and would not lead to a severe immune response within the body. In addition, the polypeptide of the present disclosure has no cytotoxicity and has long-term signal retention in vivo. It is well known that the in vivo labeling avoids many disadvantages of in vitro labeling, such as damages to the structures of tissues and cell membranes by the fixation staining method, and inability to observe intact cell. In addition, cells that have undergone in vivo staining can then be cultured and observed in vitro after elutriation, which is particularly suitable for creating novel animal models for living observation for and biological function researches of living cells.

Thirdly, the polypeptide of the present disclosure has high biocompatibility, easy penetration of tissues, and faster plasma clearance rate, and can h exhibit better pharmacokinetic properties by appropriate structural modification.

Fourthly, the polypeptide of the present disclosure may link to a reporter with little effect on the activity of the polypeptide. The polypeptide can still maintain its activity after being subjecting to severe chemical modifications and labeling. Thus, the polypeptide, linked with the reporter, of the present disclosure can perform one-step labeling on living cells, cultured cells, tissue sections, smears, and cell-climbing slides.

Finally, the small molecular polypeptide or probe of the present disclosure is can be easily obtained from chemical synthesis, and thus can be mass-prepared with accurately controlled quality.

Based on the above-mentioned advantages, the polypeptide or polypeptide-based probe of the present disclosure can be widely used to study the biological functions and activities of macrophages from cells and tissues of various animals, and can also be used for in vivo labeling, fluorescence or microscopic imaging, and the like. Based on the features of the polypeptide-based probe of the present disclosure, such as non-cytotoxicity, sensitivity, high efficiency, and selective staining, it provides a convenient and fast approach to perform direct fluorescent staining and other cell imaging processes on for example, in vivo, or ex vivo tissues, in vitro cultured cells, and the like.

BRIEF DESCRIPTION OF THE DRAWINGS

Figure 1:
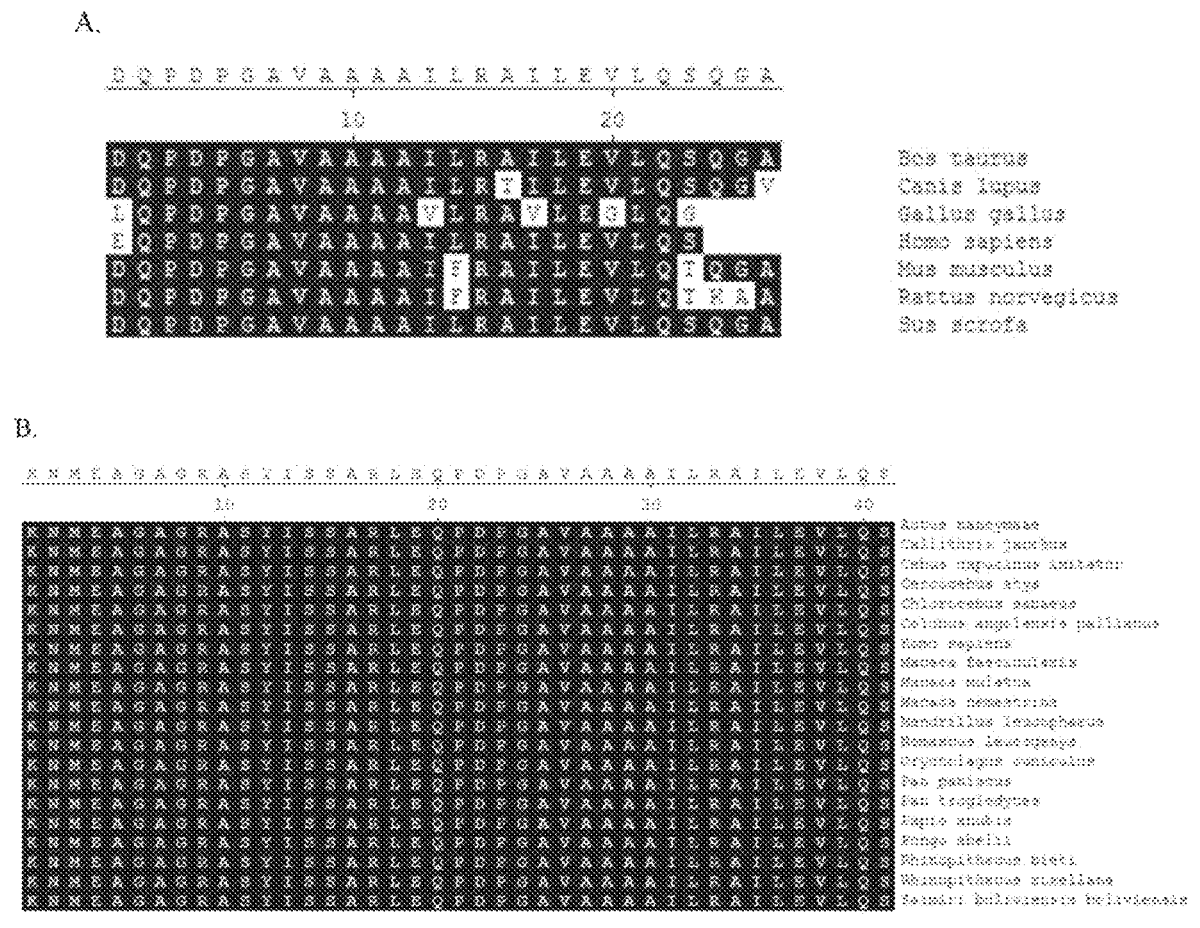

FIG. 1 shows the high homology of the C-terminal fragments of Triokinase/FMN cyclases among different animal species. FIG. 1A shows that the C-terminal fragments of the Triokinase/FMN cyclases are highly conserved among different species. FIG. 1B shows that the C-terminal fragments of the Triokinase/FMN cyclase proteins have 100% sequence identity among 20 mammalian species.

FIG. 3A is an EK24-labeled image (shown in red in the original fluorescence color image), and FIG. 3B is a nuclear-staining image obtained by using Nucblue (shown in blue in the original fluorescence color image), and FIG. 3C is a merged image of FIGS. 6A and 6B.

FIGS. 4A and 4B show fluorescent labeled images obtained by using EK24 probe and F4/80 antibody, respectively. FIG. 4C is a merged image of FIGS. 7A and 7B.

FIG. 5A shows a direct fluorescently labeled image of macrophages from a rat abdominal cavity obtained by using the EK24 fluorescent probe. FIG. 5B shows a fluorescent labeled image of cultured macrophages isolated from rat peritoneal cavity with EK24 probe.

FIG. 9A is a labeled image obtained by using EK24 fluorescent probe, and FIG. 9B is a nuclear-staining image obtained by using Nucblue, and FIG. 9C is a merged image of FIGS. 9A and 9B.

FIG. 10A is a fluoresent labeled image obtained by using the KS24 fluorescent probe (shown in red in the original fluorescence color image), and FIG. 10B is a nuclear-staining image obtained by using Nucblue (shown in blue in the original fluorescence color image), and FIG. 10C is a merged image of FIGS. 10A and 10B.

FIG. 11A is a d-KV27-labeled image (shown in red in the original fluorescence color image), and FIG. 11B is a nuclear-staining image with Nucblue (shown in blue in the original fluorescence color image), and FIG. 11C is a merged image of FIGS. 11A and 11B.

FIG. 12A is a d-KV27-labeled image (shown in red in the original fluorescence color image), and FIG. 12B is a nuclear-staining image with Nucblue (shown in blue in the original fluorescence color image), and FIG. 12C is a merged image of FIGS. 12A and 12B.

FIG. 13A is a TS42-labeled image (shown in green in the original fluorescence color image), and FIG. 13B is a nuclear-staining image with Nucblue (shown in blue in the original fluorescence color image), and FIG. 13C is a merged image of FIGS. 13A and 13B.

FIG. 14A is a KnNL36-labeled image (shown in red in the original fluorescence color image), and FIG. 14B is a nuclear-staining image with Nucblue (shown in blue in the original fluorescence color image), and FIG. 14C is a merged image of FIGS. 14A and 14B.

FIG. 15A is a LK24-labeled image (shown in red in the original fluorescence color image), and FIG. 15B is a nuclear-staining image with Nucblue (shown in blue in the original fluorescence color image), and FIG. 15C is a merged image of FIGS. 15A and 15B.

FIG. 16A is a LEK21-labeled image (shown in red in the original fluorescence color image), and FIG. 16B is a nuclear-staining image with Nucblue (shown in blue in the original fluorescence color image), and FIG. 16C is a merged image of FIGS. 16A and 16B.

FIG. 17A is a r-KA27-labeled image (shown in red in the original fluorescence color image), and FIG. 17B is a nuclear-staining image with Nucblue (shown in blue in the original fluorescence color image), and FIG. 17C is a merged image of FIGS. 17A and 17B.

FIGS. 18A, 18B, 18C, and 18D show KS24-labeled images to incubate for 10 min, 20 min, 40 min and 80 min, respectively. In FIGS. 18A, 18B, 18C, and 18D, i) is a KS24-labeled image (shown in red in the original fluorescence color image), and ii) is a nuclear-staining image with Nucblue (shown in blue in the original fluorescence color image), and iii) is a merged image of i) and ii).

FIG. 19A is a EK24-labeled image (shown in red in the original fluorescence color image), FIG. 19B is a CD68 antibody labeled image (shown in green in the original fluorescence color image), FIG. 19C is a nuclear-staining image with Nucblue (shown in blue in the original fluorescence color image), and FIG. 19D is a merged image of FIGS. 19A, 19B, and 19C.

DETAILED DESCRIPTION

Hereafter, the present disclosure will be described in detail with reference to the specific embodiments. However, it should be understood that the present disclosure will not be limited to the following embodiments. The protection scope of the present disclosure is defined by the appended claims, and the following embodiments of the present disclosure can be arbitrarily changed and combined without departing from the scope of the present disclosure.

Example 1 Preparation of EK24 Fluorescent Probe

The polypeptides used in herein were obtained by means of conventional solid phase peptide chemical synthesis using a CEM fully automated microwave peptide synthesizer according to operating instructions provided by the supplier. The polypeptides used herein were derived from the C-terminal fragment of human or non-human Triokinase/FMN cyclases.

In this example, the polypeptide having the following amino acid sequence was synthesized: EQPDP-GAVAAAAILRAILEVLQSK (SEQ ID NO:11).

According to the manufacturer's instructions, the synthesized polypeptide was mixed with a reaction reagent of HOOK™ Dye Rhodamine Labeling Kit (Cat. #786-142, Biosciences), adjusted the pH, reacted for 1-2 hours, purified by HPLC to obtain the EK24 fluorescence probe. The chemical structure of the obtained fluorescent probe is as follows:

(SEQ ID NO: 3)
EQPDPGAVAAAAILRAILEVLQS-Y (EK24), wherein, Y is a lysine+a fluorescent reporter, which is a rhodamine fluorescent labeling group linked to an amino group on the side chain of lysine.

Example 2 Preparation of EK24 Fluorescent Probe Solution 1 mg of EK24 fluorescent probe was dissolved in 87 μL of DMSO (dimethyl sulfoxide), which was then added to 6873 μL serum-free DMEM (Hyclone) medium, mixing well to give 50 μM of EK24 fluorescent probe solution. As required, 50 μM of EK24 fluorescent probe solution can be diluted by adding the serum-free DMEM medium during use.

Example 3 In Vitro Fluorescence Labeled Staining of a Mouse Macrophage Cell Line Culture the mouse macrophage cell line RAW264.7 in a 96-well plate, wash the wells once with 1×PBS buffer or a serum-free DMEM incomplete medium, remove the washing liquid, add EK24 solution of 10 μM which had been diluted with 100 μL of serum-free DMEM incomplete medium, and incubate in a cell culture incubator for 1 h. After that, wash the wells twice with 1×PBS buffer or the serum-free DMEM incomplete medium. Then, add DMEM complete medium containing 10% FBS and 1% streptomycin-penicillin, and double-stain the cells using nuclear dye Nucblue, and observe under EVOS® FL Auto fluorescence microscope (Life Technologies, light source 10%, exposure 200 ms, gain 5). The results are shown in FIG. 2.

Figure 2:
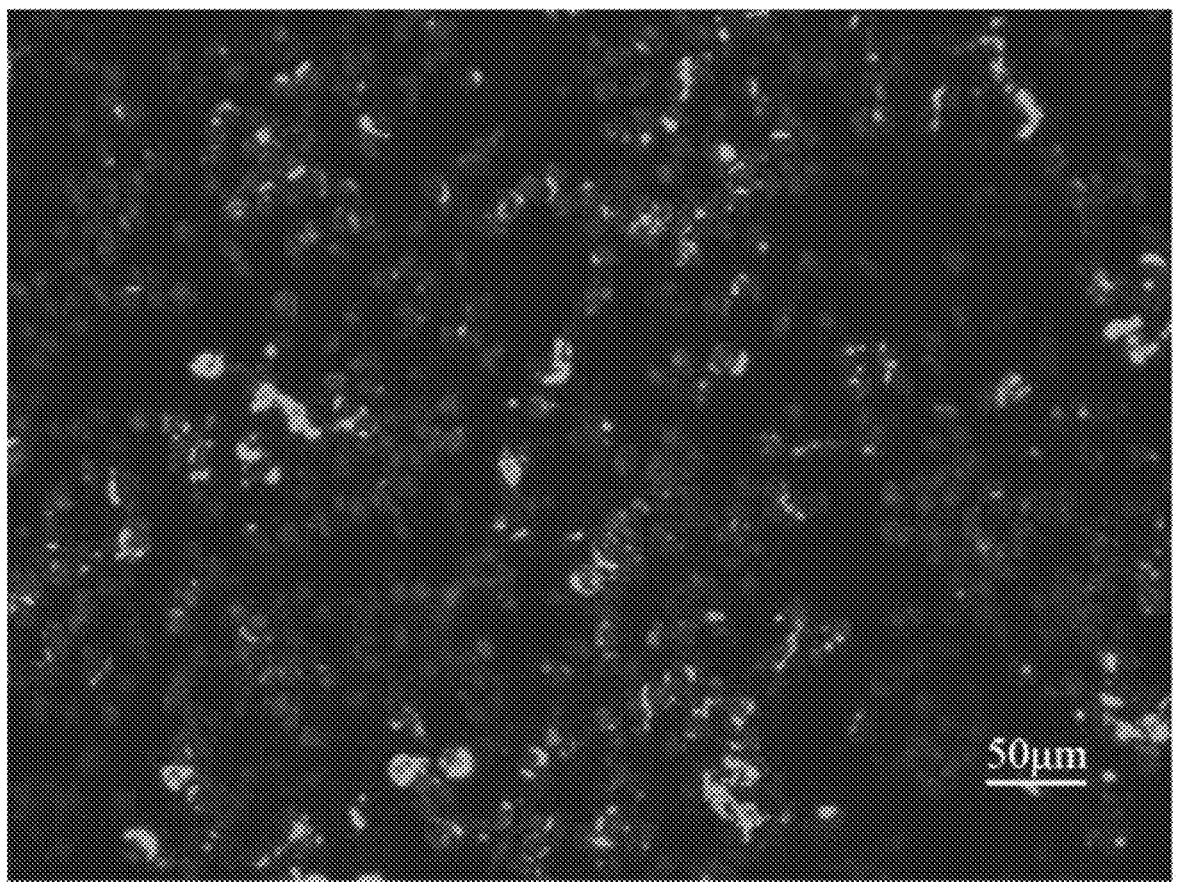
FIG. 2 shows in vivo fluorescent labeled image obtained by staining mouse macrophage cell line RAW264.7 cultured in vitro. The mouse macrophage cell line RAW264.7 was stained with EK24 probe (shown in red in the original fluorescent color image) and Nucblue (shown in blue in the original fluorescent color image).

FIG. 2 shows images of in vitro cultured mouse macrophage cell line that were fluorescent labeled using the EK24 fluorescent probe (shown in red in the original fluorescence color image) and Nucblue (shown in blue in the original fluorescence color image).

It can be seen from FIG. 2 that the macrophage cell line RAW264.7 can be labeled with the EK24 fluorescent probe (shown in red in the original fluorescence color image).

Example 4 In Vivo Fluorescent Labeling Macrophages in a Mouse Abdominal Cavity with EK24 Fluorescent Probe Dilute 300 μL of 50 μM EK24 fluorescent probe solution with serum-free DMEM incomplete medium to obtain 1 mL of solution, then inject into the abdominal cavity of 5-8 weeks old Kunming mice. After 4 hours, inject 5 mL of 1×PBS and massage. After 10 minutes, sacrifice the mice by cervical vertebra dislocation. Cut the abdominal cavity skin of the mice, pierce the abdominal wall muscle by a syringe, and extract the fluid in the abdominal cavity of the mice. Centrifuge the extracted peritoneal fluid at 1000 rpm for 5 min, wash twice with 1×PBS. Add appropriate amount of cells to a 96-well plate and double-stain with a nuclear dye Nucblue (Invitrogen). Observe under fluorescence microscope (light source 10%, exposure 200 ms, gain 5) after the suspended cells were settled down at the bottom of the plate. The results are shown in FIG. 3.

FIG. 3A is an EK24-labeled image (shown in red in the original fluorescence color image), FIG. 2B is a nuclear-staining image obtained by using Nucblue (shown in blue in the original fluorescence color image), FIG. 3C is a merged image of FIGS. 3A and 3B.

Figure 3:
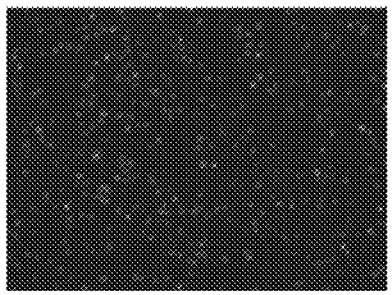
FIG. 3 shows in vivo fluorescent labeled image obtained by staining macrophages in a mouse abdominal cavity with EK24 fluorescent probe. The mouse peritoneal macrophages were first labeled with the EK24 fluorescent probe in vivo, and then removed from the mouse peritoneal cavity for Nucblue staining.
Figure 3:
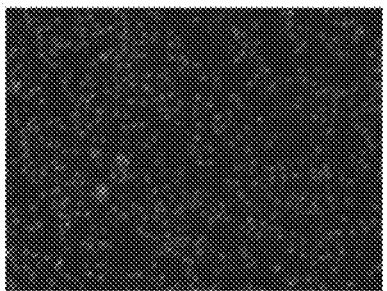
Figure 3:
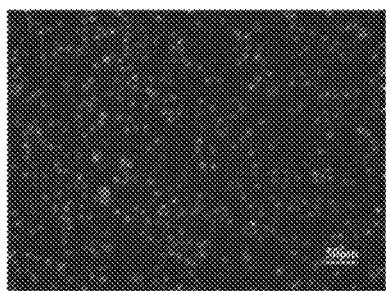

It can be seen from FIG. 3 that the macrophages extracted from the mouse abdominal cavity can be labeled with the EK24 fluorescent probe (shown in red in the original fluorescence color image).

Figure 4:
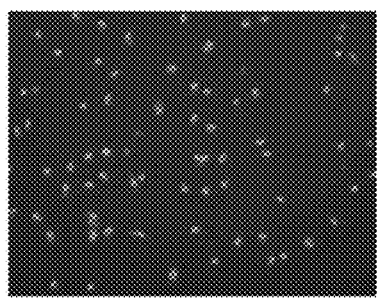
FIG. 4 shows fluorescent labeled image obtained by staining macrophages, which were removed from the mouse abdominal cavity and cultured in vitro.
Figure 4:
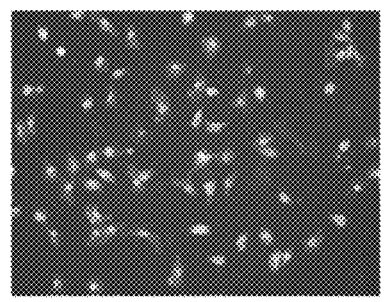
Figure 4:
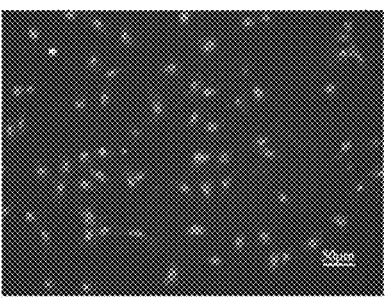

Example 5 In Vitro Fluorescent Labeling of Cultured Macrophages Isolated from Mouse Peritoneal Cavity by EK24 Probe Inject 5 mL of serum-free DMEM incomplete medium into the abdominal cavity of 5 to 8 weeks old mice, massage the abdominal cavity gently for 10 min, and sacrifice the mice by cervical vertebra dislocation. Extract the fluid from the abdominal cavity gently with a syringe, inject into a 5 mL centrifuge tube and centrifuge at 1000 rpm for 5 min, remove the supernatant, and resuspend the collected ex-vivo cells in DMEM/F12 medium containing 10% FBS, then add into a 96-well plate for culture. Generally, if cells are taken intraperitoneally for in vitro culture, macrophages would tend to adhere to bottom of the well, and other cells would be washed off. The cells were cultured for more than 2 days until the cells attached the bottom firmly. At this time, the cells remaining in the wells were basically macrophages. Select two wells, one as a control and the other as an experimental well. The cells of the control were nuclear stained with Nucblue. The experimental well was added with a premix of AlexaFluor®488 anti-mouse F4/80 antibody (Biolegend) and EK24 fluorescent probe, and then incubated for 1 h at 37° C. The premix contained 10 μM of EK24 solution and 2 μL of Alexa Fluor®488 anti-mouse F4/80 antibody diluted with 100 μL of serum-free DMEM incomplete medium. The remaining treatment steps can refer to Example 4. The cells were observed under a fluorescence microscope (20×objective lens, light source 10%, exposure 200 ms, gain 5). The results are shown in FIG. 4.

FIG. 4A shows a fluorescent labeled image obtained by using EK24 fluorescent probe (shown in red in the original fluorescence color image) and nuclear stained image obtained by using Nucblue (shown in blue in the original fluorescence color image).

FIG. 4B shows a fluorescent labeled image obtained by using the F4/80 antibody (shown in green in the original fluorescence color image) and nuclear stained image obtained by using Nucblue (shown in blue in the original fluorescence color image). F4/80 antigen is currently recognized as a surface characteristic marker of mouse peritoneal macrophages. It can be seen from FIG. 4B that almost all the cells obtained by intraperitoneal massage were labeled with F4/80 antibody, indicating that these labeled cells were macrophages.

FIG. 4C is a merged image of FIGS. 4A, and 4B. From this figure, it can be seen that both the EK24 fluorescent probe label and the F4/80 antibody label are co-localized on the same cells. This result indicates that cells labeled with the F4/80 antibody are also labeled with the EK24 fluorescent probe, which further indicates that the EK24 fluorescent probe can target and recognize macrophages.

Example 6 In Vitro Fluorescent Labeling of Primary Macrophages from Rat Peritoneal Cavity by EK24 Fluorescent Probe With the same process as in Example 5, extract cells from the abdominal cavity of 5 to 8 weeks old SD rats using 20 mL serum-free DMEM incomplete medium and culture the cells in a 96-well plate. After culturing for more than 2 days, until the cells attached the bottom firmly, a well was selected and added with EK24 fluorescent probe for incubation. Then the cells were observed under a fluorescence microscope (20×, light source 10%, exposure 200 ms, gain 5). The results are shown in FIG. 5.

FIG. 5A shows images obtained from direct fluorescent labeling of macrophages from a rat abdominal cavity with EK24 fluorescent probe (shown in red in the original fluorescence color image) and Nucblue (shown in blue in the original fluorescence color image). FIG. 5B shows images obtained by fluorescent labeling of primary macrophages, which were taken from rat peritoneal cavity and cultured for more than 2 days in vitro with EK24 fluorescent probe (shown in red in the original fluorescence color image) and Nucblue (shown in blue in the original fluorescence color image).

Figure 5:
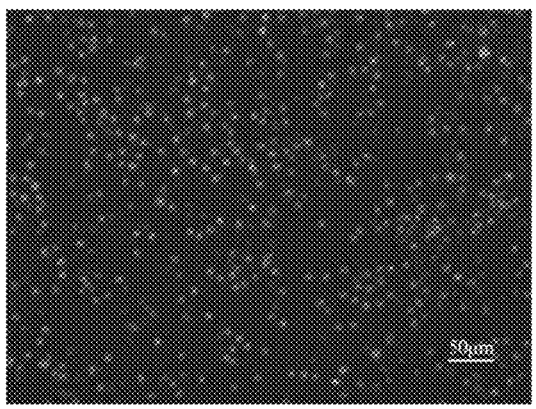
FIG. 5 shows fluorescent labeled image obtained by staining macrophages from rat peritoneal cavity with EK24 fluorescent probe.
Figure 5:
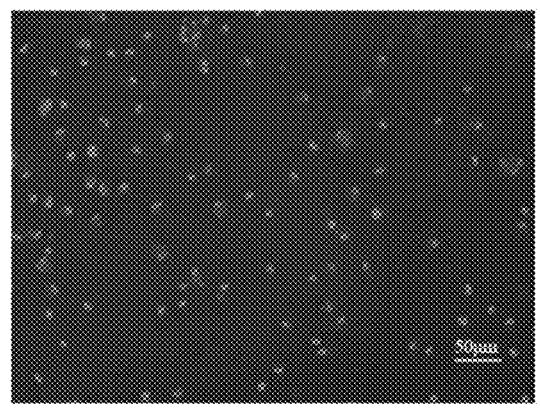

It can be seen from FIG. 5 that the EK24 fluorescent probe can effectively label the in vitro cultured primary macrophages from rat peritoneal cavity.

Example 7 In Vitro Fluorescence Labeling of Mouse Primary Monocyte Precursors by EK24 Probe As described above, macrophages were derived from monocytes in blood, and monocytes were transformed from monocyte precursors in bone marrow. In order to verify whether the EK24 fluorescent probe can recognize monocyte precursors, the EK24 fluorescent probe and Nucblue were used to label monocytes from the mesenchyme of bone marrow.

In a bio-safety hood, take the femur of a Kunming mice, cut off both ends of the femur, wash medulla out with PBS, and collect cells by centrifugation. The collected ex-vivo cells were resuspended in F12/DMEM medium containing 10% FBS and 1% streptomycin-penicillin, and add it to a 96-well plate for culture. After culturing for more than 2 days, until the cells attached the bottom firmly, the cells remaining in the wells were basically monocyte precursors. Treat with reference to Example 5. Then the cells were observed under a fluorescence microscope (200×, light source 50%, exposure 200 ms, gain 5). The results are shown in FIG. 6.

Figure 6:
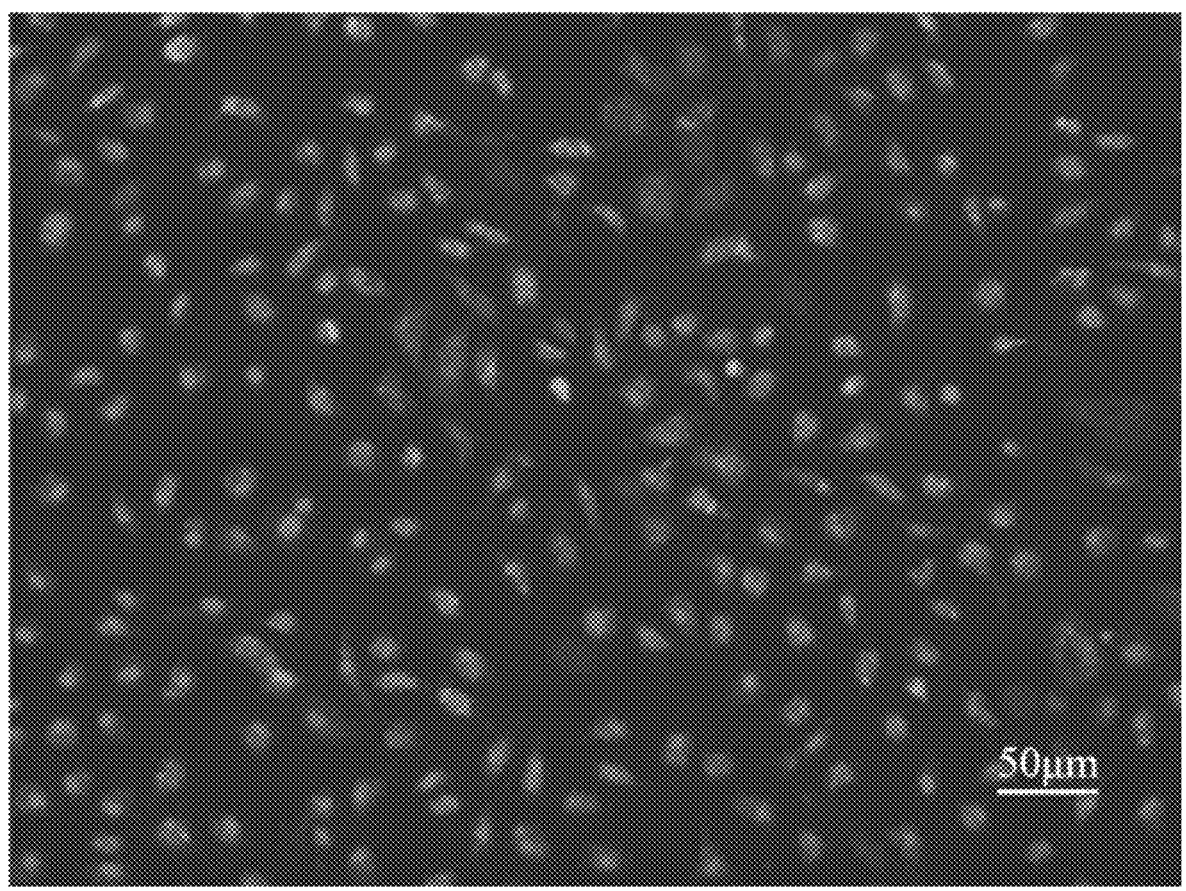
FIG. 6 shows a fluorescent labeled image obtained by staining cultured monocyte precursors isolated from mouse bone marrow using, with EK24 fluorescent probe (shown in red in the original fluorescent color image) and Nucblue (shown in blue in the original fluorescent color image).

FIG. 6 shows images obtained with direct fluorescent labeling of monocyte precursors from the mesenchyme of mouse with EK24 fluorescent probe (shown in red in the original fluorescence color image) and Nucblue (shown in blue in the original fluorescence color image). It can be seen that the EK24 fluorescent probe (shown in red in the original fluorescence color image) is capable of labeling monocyte precursors from the mesenchyme of mouse bone marrow.

Example 8 In Vitro Fluorescent Labeling of Rat Primary Monocyte Precursors by EK24 Fluorescent Probe With a similar process to Example 7, mononuclear cell precursors from rat femoral bone marrow were taken and cultured, and then labeled by using EK24 fluorescent probe and Nucblue. Then the cells were observed under a fluorescence microscope (20×, light source 10%, exposure 200 ms, gain 5). The results are shown in FIG. 7.

Figure 7:
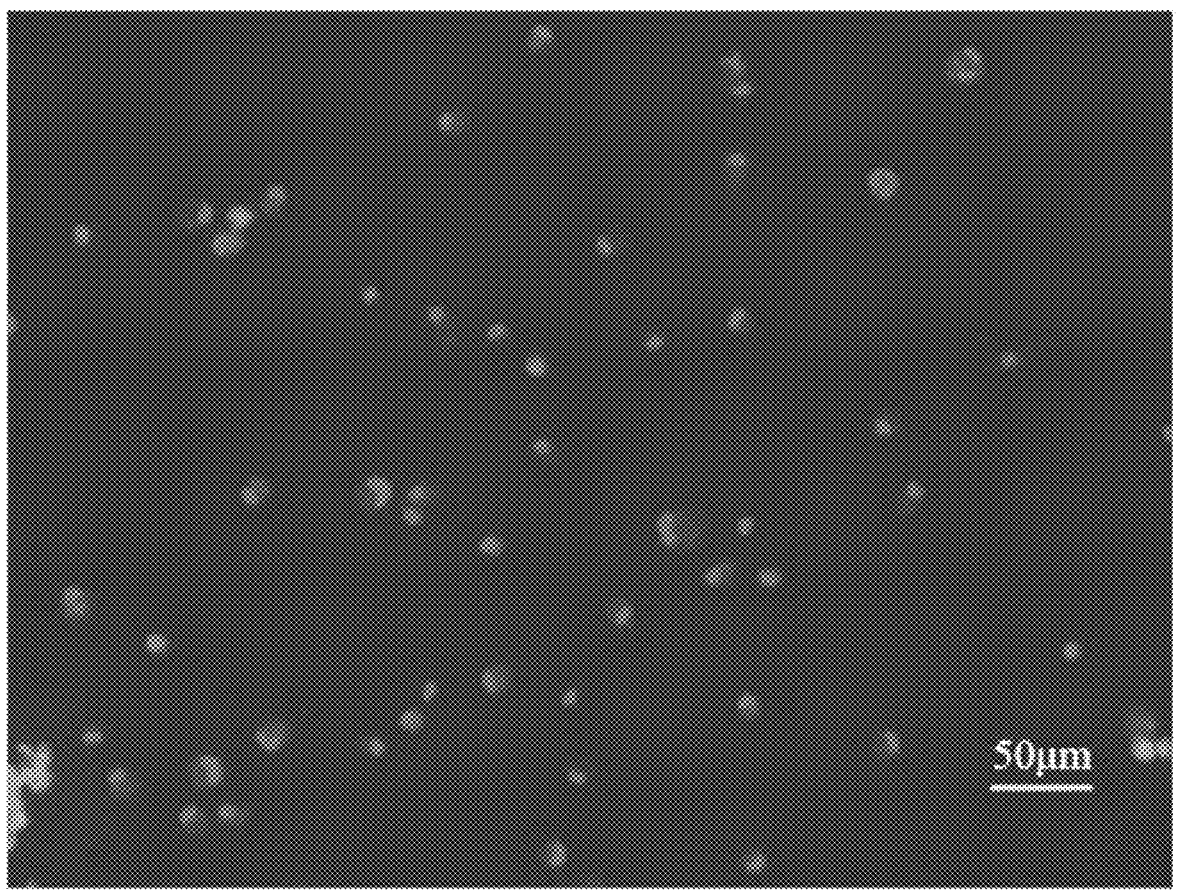
FIG. 7 shows a fluorescent labeled image obtained by staining cultured monocyte precursors isolated from rat bone marrow, with EK24 fluorescent probe (shown in red in the original fluorescence color image) and Nucblue (shown in blue in the original fluorescence color image).

FIG. 7 shows images obtained by fluorescent labeling of monocyte precursors from rat bone marrow mesenchyme with EK24 fluorescent probe (shown in red in the original fluorescence color image) and Nucblue (shown in blue in the original fluorescence color image). It can be seen that the EK24 fluorescent probe (shown in red in the original fluorescence color image) is also capable of labeling monocyte precursors from rat bone marrow mesenchyme.

Example 9 In Vitro Fluorescent Labeling of Primary Monocyte Precursors of New Zealand White Rabbit by EK24 Fluorescent Probe With a similar process to Example 7, bone marrow monocyte precursors of New Zealand White Rabbit were taken and cultured, then labeled by using EK24 fluorescent probe and Nucblue. Then the cells were observed under a fluorescence microscope (20×, light source 10%, exposure 200 ms, gain 5). The results are shown in FIG. 8.

Figure 8:
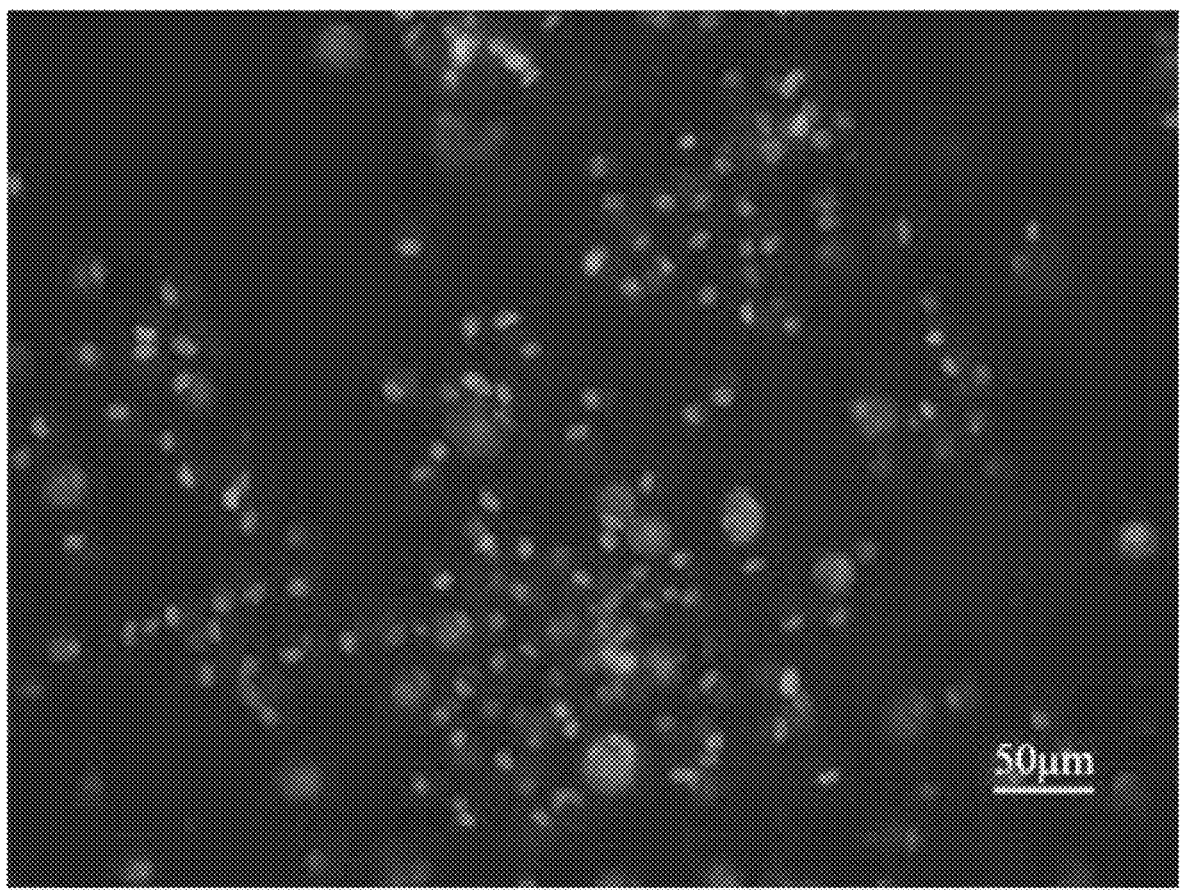
FIG. 8 shows a fluorescent labeled image obtained by staining cultured monocyte precursors isolated from New Zealand White Rabbit bone marrow, with EK24 fluorescent probe (shown in red in the original fluorescence color image) and Nucblue (shown in blue in the original fluorescence color image).

FIG. 8 shows images obtained from directly fluorescent labeling of monocyte precursors from mesenchyme of New Zealand White Rabbit bone marrow with the EK24 fluorescent probe (shown in red in the original fluorescence color image) and Nucblue (shown in blue in the original fluorescence color image). It can be seen that the EK24 fluorescent probe (shown in red in the original fluorescence color image) is also capable of labeling monocyte precursors from New Zealand White Rabbit bone marrow mesenchyme.

Figure 9:
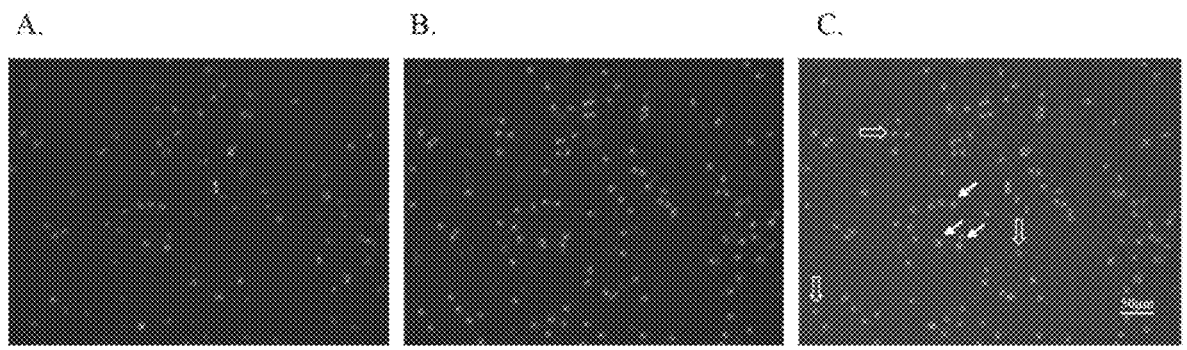
FIG. 9 shows fluorescent labeled image obtained by staining cultured peritoneal macrophages and mesenteric digestive cells with EK24 fluorescent probe.

Example 10 EK24 Fluorescent Probe Selective Labeling and Staining of Cultured Peritoneal Macrophages Among Other Cells Released from Enzyme-Digested Mesenterium Take 5 to 8 week-old Kunming mice, inject intraperitoneally with 5 mL of serum-free DMEM incomplete medium. After 1 hour, sacrifice the mice by cervical vertebra dislocation. Make an incision on the skin of abdominal cavity, pierce the abdominal wall muscle using a syringe, and extract the fluid in the abdominal cavity of the mice. Wash twice with 1×PBS, collect peritoneal cells by centrifugation. Also take the mesenteries of the Kunming mice and purge twice with 1×PBS in centrifuge tubes. Incubate the obtained peritoneal cells and mesenteries in 0.25% trypsin solution and digest for 30 minutes. Enrich the cells by centrifugation, and then culture for 3 days in a 96-well plate using F12/DMEM culture solution containing 10% FBS and 1% streptomycin-penicillin. Referring to Example 5, label with the EK24 fluorescent probe and Nucblue. Then the cells were observed under a fluorescence microscope (20×, light source 10%, exposure 200 ms, gain 5). The results are shown in FIG. 9.

FIG. 9A is an image obtained by labeling with EK24 fluorescent probe (shown in red in the original fluorescence color image), and FIG. 9B is an image obtained by nuclear-staining with Nucblue (shown in blue in the original fluorescence color image), and FIG. 9C is a merged image of FIGS. 9A and 9B. It can be seen from the figures that the EK24 fluorescent probe only stains macrophages (as shown by the solid arrow in FIG. 12C, cells labeled with both blue and red fluorescences), and not stain non-macrophages (as shown by the hollow arrow in FIG. 12C, cells labeled with only blue fluorescence but no red fluorescence).

Example 11 Fluorescent Labeling of Macrophages by the Probes which are Derived from the C-Terminal Fragmentses of Triokinases/FMN Cyclases of Different Mammal Species Table 1 lists probes, which contain the polypeptide fragments from the C-terminal fragments of Triokinases/FMN cyclases of different species and were prepared by a similar process as described in Examples 1 and 2, and in vivo imaging results of mouse peritoneal macrophages using these probes.

TABLE 1

Probes from C-terminal fragments of Triokinases/FMN cyclases of different animal species and in vivo imaging results of mouse peritoneal macrophages using the probes.

Figure 10:
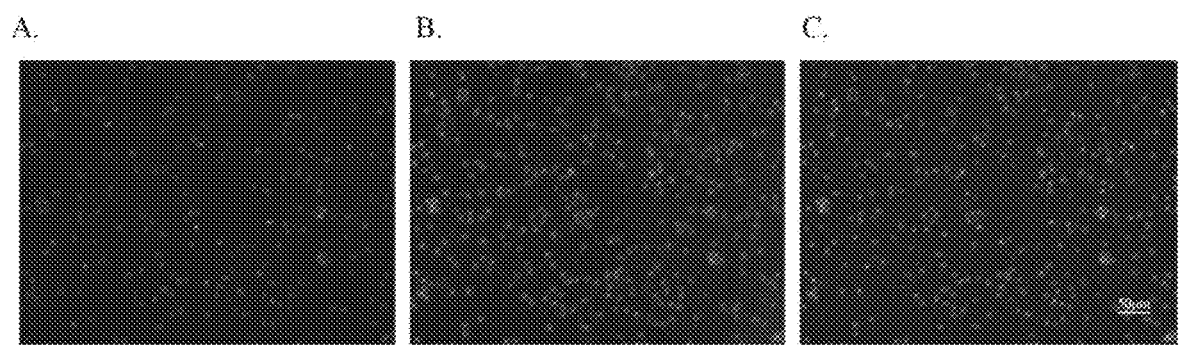
FIG. 10 shows in vivo fluorescent labeled image obtained by staining macrophages in a mouse abdominal cavity with KS24 fluorescent probe. The mouse peritoneal macrophages were first labeled with the KS24 fluorescent probe in vivo, and then removed from mouse peritoneal cavity for Nucblue staining.
Figure 11:
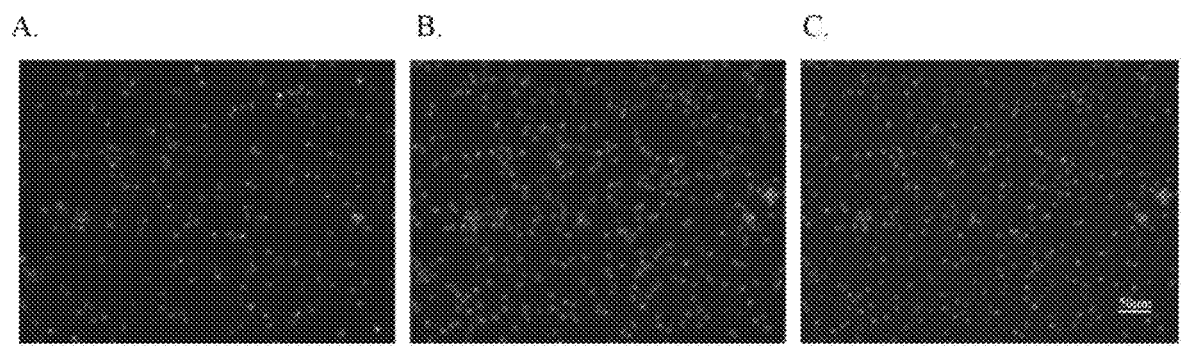
FIG. 11 shows in vivo fluorescent labeled image obtained by staining macrophages in a mouse abdominal cavity with d-KV27 fluorescent probe. The mouse peritoneal macrophages were first labeled with d-KV27 fluorescent probe in vivo, and then removed from mouse peritoneal cavity for Nucblue staining.
Figure 12:
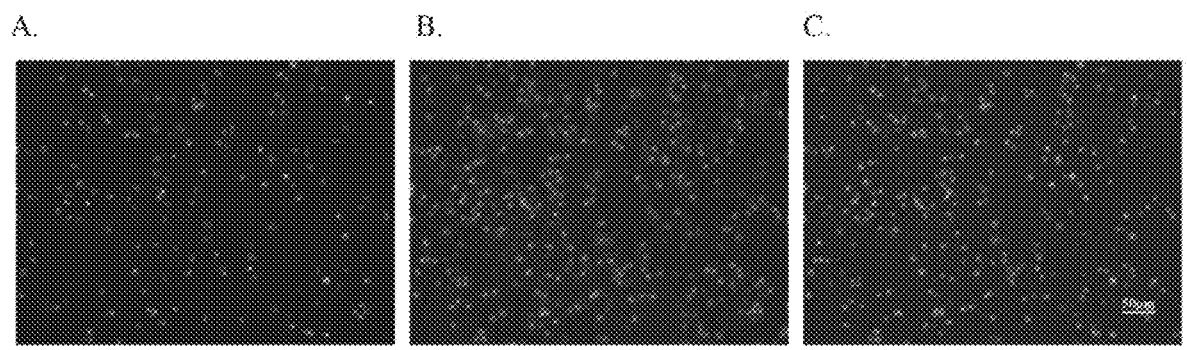
FIG. 12 shows in vivo fluorescent labeled image obtained by staining macrophages in a mouse abdominal cavity with d-KV27 fluorescent probe. The mouse peritoneal macrophages were first labeled with d-KV27 fluorescent probe in vivo, and then removed from mouse peritoneal cavity for Nucblue staining.
Figure 13:
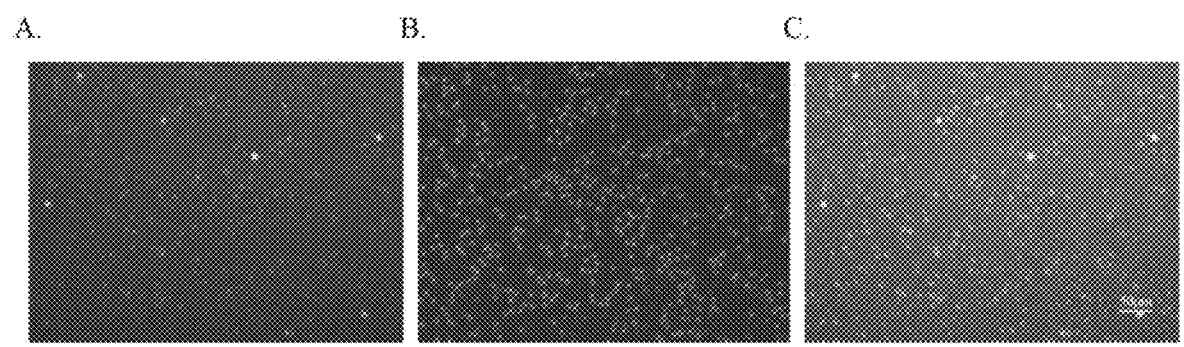
FIG. 13 shows in vivo fluorescent labeled image obtained by staining macrophages in a mouse abdominal cavity with TS42 fluorescent probe. The mouse peritoneal macrophages were first labeled with the TS42 fluorescent probe in vivo, and then removed from mouse peritoneal cavity for Nucblue staining.
Figure 14:
FIG. 14 shows in vivo fluorescent labeled image obtained by staining macrophages in a mouse abdominal cavity with KnNL36 fluorescent probe. The mouse peritoneal macrophages were first labeled with the KnNL36 fluorescent probe in vivo, and then removed from mouse peritoneal cavity for Nucblue staining.
Figure 15:
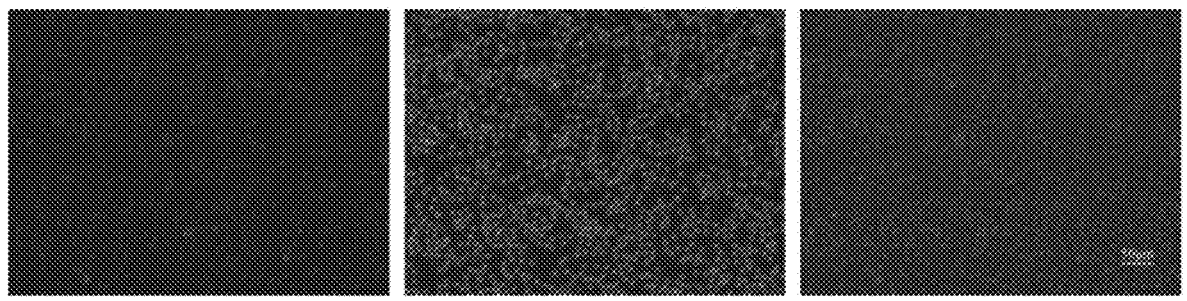
FIG. 15 shows in vivo fluorescent labeled image obtained by staining macrophages in a mouse abdominal cavity with LK24 fluorescent probe. The mouse peritoneal macrophages were first labeled with the LK24 fluorescent probe in vivo, and then removed from mouse peritoneal cavity for Nucblue staining.
Figure 16:
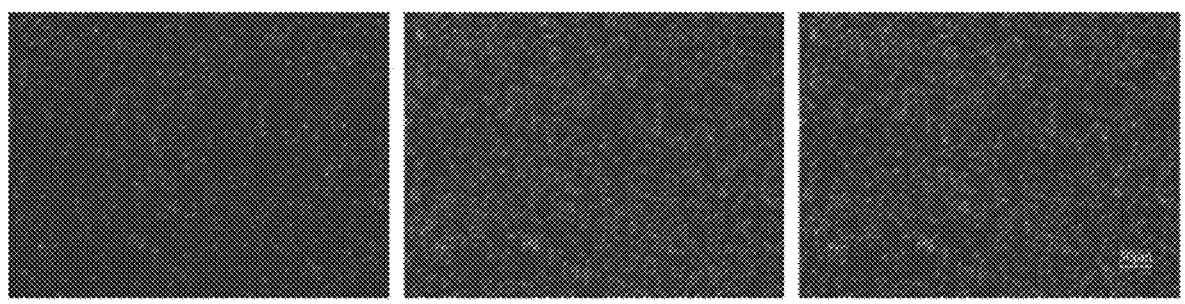
FIG. 16 shows in vivo fluorescent labeled image obtained by staining macrophages in a mouse abdominal cavity with LEK21 fluorescent probe. The mouse peritoneal macrophages were first labeled with LEK21 fluorescent probe in vivo, and then removed from mouse peritoneal cavity for Nucblue staining.
Figure 17:
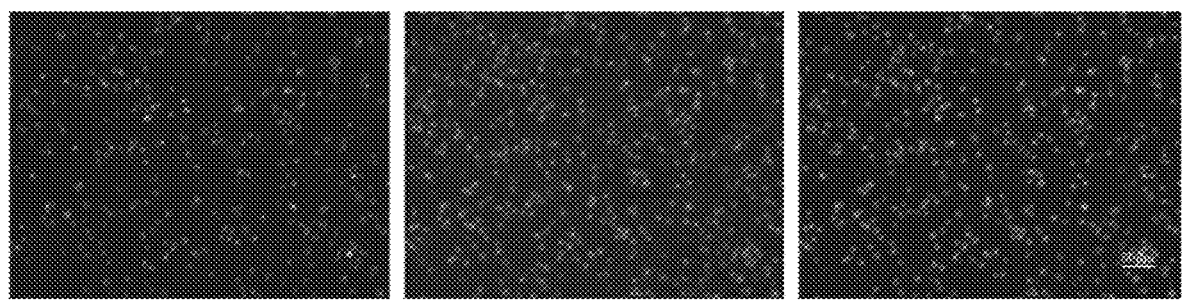
FIG. 17 shows in vivo fluorescent labeled image obtained by staining macrophages in a mouse abdominal cavity with r-KA27 fluorescent probe. The mouse peritoneal macrophages were first labeled with r-KA27 fluorescent probe in vivo, and then removed from mouse peritoneal cavity for Nucblue staining.

| Species | Sequence | In vivo targeted imaging effect | Figure | Name |
|---|---|---|---|---|
| Chickens (Gallus gallus) | LQPDPGAVA AAAVLRAVL EGLQG-Y (SEQ ID NO.: 6) | + | FIG. 15 | LK24 |
| Rats (Rattus norvegicus) | X-DQPDPGA VAAAAIFRA ILEVLQTKA A (SEQ ID NO.: 7) | +++ | FIG. 17 | r-KA27 |
| Dogs (canis lupus) | X-DQPDPGA VAAAAILRT ILEVLQSQG V (SEQ ID NO.: 8) | ++ | FIG. 11 | d-KV27 |
| Pigs (sus scrofa) | X-DQPDPGA VAAAAILRA ILEVLQSQG A (SEQ ID NO.: 9) | +++ | FIG. 12 | b-KA27 |
| Cattles (bos taurus) | X-DQPDPGA VAAAAILRA ILEVLQSQG A (SEQ ID NO.: 9) | +++ | FIG. 12 | b-KA27 |
| Rhesus monkeys (macaca mulatta) | EDQPDPGAV AAAAILRAI LEVLQS (SEQ ID NO.: 10)-Y | +++ | FIG. 2-9 | EK24 |
| Humans (Homo sapiens) | EDQPDPGAV AAAAILRAI LEVLQS (SEQ ID NO.: 10)-Y | +++ | FIG. 2-9 | EK24 |
| Humans (Homo sapiens) | X-EDQPDPG AVAAAAILR AILEVLQS (SEQ ID NO.: 10) | +++ | FIG. 10 | KS24 |
| Humans (Homo sapiens) | LEQPDPGAV AAAAILRAI LE-Y (SEQ ID NO.: 2) | + | FIG. 16 | LEK21 |
| Humans (Homo sapiens) | X-TKNMEAG AGRASYISS ARLEQPDPG AVAAAAILR AILEVLQS (SEQ ID NO.: 5) | ++ | FIG. 13 | TS42 |
| Humans (Homo sapiens) | X-KNMEAGA GRASYISSA RLEQPDPGA VAAAAILRA IL (SEQ ID NO.: 4) | ++ | FIG. 14 | KnNL36 |

X, Y = reporter or cysteine/lysine + reporter (rhodamine or FITC)

From the results in Table 1, it can be seen that all the polypeptide fragments from the C-terminal fragmentses of Triokinase/FMN cyclases of different animals can targeted recognize monocytes/macrophages. Specifically, LK24 derived from chicken Triokinase/FMN cyclase, r-KA27 derived from rat Triokinase/FMN cyclase, d-KV27 derived from dog Triokinase/FMN cyclase, b-KA27 derived from pig and cattle Triokinase/FMN cyclase, EK24 derived from rhesus monkey Triokinase/FMN cyclase and EK24, KS24, LEK21, TS42 and KnNL36 derived from human Triokinase/FMN cyclase, can effectively recognize macrophages in vivo. It indicates that highly conserved polypeptide fragments from the C-terminal fragmentses of Triokinases/FMN cyclases of different species can be used as probes to label macrophages. The following examples provide further relevant experimental results.

Example 12 Fluorescent Labeling of Macrophages in a Mouse Abdominal Cavity by KS24 Fluorescent Probe Referring to Example 4, using the same treatment process, the mouse peritoneal macrophages were first labeled in vivo using KS24 fluorescent probe, and then removed from the mouse abdominal cavity for nuclear fluorescence labeling with Nucblue. The resulted macrophages were observed under a fluorescence microscope (20×, light source 10%, exposure 200 ms, gain 5). The results are shown in FIG. 10.

FIG. 10A is a labeled image obtained by using KS24 fluorescent probe (shown in red in the original fluorescence color image), and FIG. 10B is a nuclear-staining image obtained by using Nucblue (shown in blue in the original fluorescence color image), and FIG. 10C is a merged image of FIGS. 10A and 10B.

It can be seen from FIG. 10 that the macrophages extracted from the mouse abdominal cavity can be labeled with KS24 fluorescent probe.

Example 13 Fluorescent Labeling of Macrophages in a Mouse Abdominal Cavity by d-KV27 Fluorescent Probe Referring to Example 4, using the same treatment process, the mouse peritoneal macrophages were first labeled in vivo using d-KV27 fluorescent probe, and then removed from the mouse abdominal cavity for nuclear fluorescence labeling with Nucblue. The macrophages were observed under a fluorescence microscope (20×, light source 10%, exposure 200 ms, gain 5). The results are shown in FIG. 11.

FIG. 11A is a labeled image obtained by using d-KV27 fluorescent probe (shown in red in the original fluorescence color image), and FIG. 11B is a nuclear-staining image obtained by using Nucblue (shown in blue in the original fluorescence color image), and FIG. 11C is a merged image of FIGS. 11A and 11B.

It can be seen from FIG. 11 that the macrophages extracted from the mouse abdominal cavity can be labeled with d-KV27 fluorescent probe.

Example 14 Fluorescent Labeling of Macrophages in a Mouse Abdominal Cavity by b-KA27 Fluorescent Probe Referring to Example 4, using the same treatment process, the mouse peritoneal macrophages were first labeled in vivo using b-KA27 fluorescent probe, and then removed from the mouse abdominal cavity for nuclear fluorescence labeling with Nucblue. The macrophages were observed under a fluorescence microscope (20×, light source 10%, exposure 200 ms, gain 5). The results are shown in FIG. 12.

FIG. 12A is a labeled image obtained by using b-KA27 fluorescent probe (shown in red in the original fluorescence color image), and FIG. 12B is a nuclear-staining image obtained by using Nucblue (shown in blue in the original fluorescence color image), and FIG. 12C is a merged image of FIGS. 12A and 12B.

It can be seen from FIG. 12 that the macrophages extracted from the mouse abdominal cavity can be labeled with b-KA27 fluorescent probe.

Example 15 Fluorescent Labeling of Macrophages in a Mouse Abdominal Cavity by TS42 Fluorescent Probe Referring to Example 4, using the same treatment process, the mouse peritoneal macrophages were first labeled in vivo using TS42 fluorescent probe, and then removed from the mouse abdominal cavity for nuclear fluorescence labeling with Nucblue. The macrophages were observed under a fluorescence microscope (20×, light source 50%, exposure 200 ms, gain 5). The results are shown in FIG. 13.

FIG. 13A is a labeled image obtained by using TS42 fluorescent probe (shown in green in the original fluorescence color image), and FIG. 13B is a nuclear-staining image obtained by using Nucblue (shown in blue in the original fluorescence color image), and FIG. 13C is a merged image of FIGS. 13A and 13B.

It can be seen from FIG. 13 that the macrophages extracted from the mouse abdominal cavity can be labeled with TS42 fluorescent probe.

Example 16 Fluorescent Labeling of Macrophages in a Mouse Abdominal Cavity by KnNL36 Fluorescent Probe Referring to Example 4, using the same treatment process, the mouse peritoneal macrophages were first labeled in vivo using KnNL36 fluorescent probe, and then removed from the mouse abdominal cavity for nuclear fluorescence labeling with Nucblue. The macrophages were observed under a fluorescence microscope (20×, light source 10%, exposure 200 ms, gain 5). The results are shown in FIG. 14.

FIG. 14A is a labeled image obtained by using KnNL36 fluorescent probe (shown in red in the original fluorescence color image), and FIG. 14B is a nuclear-staining image obtained by using Nucblue (shown in blue in the original fluorescence color image), and FIG. 14C is a merged image of FIGS. 14A and 14B.

It can be seen from FIG. 14 that the macrophages extracted from the mouse abdominal cavity can be labeled with KnNL36 fluorescent probe.

Example 17 Fluorescent Labeling of Macrophages in a Mouse Abdominal Cavity by LK24 Fluorescent Probe Referring to Example 4, using the same treatment process, the mouse peritoneal macrophages were first labeled in vivo using LK24 fluorescent probe, and then removed from the mouse abdominal cavity for nuclear fluorescence labeling with Nucblue. The macrophages were observed under a fluorescence microscope (20×). The results are shown in FIG. 15.

FIG. 15 shows the image observed under a fluorescence microscope (light source 50%, exposure 200 ms, gain 5). Wherein FIG. 15A is a labeled image obtained by using LK24 fluorescent probe (shown in red in the original fluorescence color image), and FIG. 15B is a nuclear-staining image obtained by using Nucblue (shown in blue in the original fluorescence color image), and FIG. 15C is a merged image of FIGS. 15A and 15B.

It can be seen from FIG. 15 that the macrophages extracted from the mouse abdominal cavity can be labeled with LK24 fluorescent probe.

Example 18 Fluorescent Labeling of Macrophages in a Mouse Abdominal Cavity Using LEK21 Fluorescent Probe Referring to Example 4, using the same treatment process, the mouse peritoneal macrophages were first labeled in vivo using LEK21 fluorescent probe, and then removed from the mouse abdominal cavity for nuclear fluorescence labeling with Nucblue. The macrophages were observed under a fluorescence microscope (20×). The results are shown in FIG. 16.

FIG. 16 shows the image observed under a fluorescence microscope (light source 50%, exposure 200 ms, gain 5). Wherein FIG. 16A is a labeled image obtained by using LEK21 fluorescent probe (shown in red in the original fluorescence color image), and FIG. 16B is a nuclear-staining image obtained by using Nucblue (shown in blue in the original fluorescence color image), and FIG. 16C is a merged image of FIGS. 16A and 16B.

It can be seen from FIG. 16 that the macrophages extracted from the mouse abdominal cavity can be labeled with LEK21 fluorescent probe.

Example 19 Fluorescent Labeling of Macrophages in a Mouse Abdominal Cavity by r-KA27 Fluorescent Probe Referring to Example 4, using the same treatment process, the mouse peritoneal macrophages were first labeled in vivo using r-KA27 fluorescent probe, then removed from the mouse abdominal cavity for nuclear fluorescence labeling with Nucblue. The macrophages were observed under a fluorescence microscope (20×, light source 10%, exposure 200 ms, gain 5). The results are shown in FIG. 17.

FIG. 17A is a labeled image obtained by using r-KA27 fluorescent probe (shown in red in the original fluorescence color image), and FIG. 17B is a nuclear-staining image obtained by using Nucblue (shown in blue in the original fluorescence color image), and FIG. 17C is a merged image of FIGS. 17A and 17B.

It can be seen from FIG. 17 that the macrophages extracted from the mouse abdominal cavity can be labeled with r-KA27 fluorescent probe.

Example 20 Fluorescence Labeling of Primary Monocyte Precursors of Mouse by KS24 Fluorescent Probe at Different Incubation Times Referring to Example 7, using the same treatment process, the monocyte precursors from mouse bone marrow were obtained. After culturing for 6 days, the cultured cells were labeled with KS24 fluorescent probe over different incubation times. Then the cells were observed under a fluorescence microscope (20×, light source 20%, exposure 200 ms, gain 5). The results are shown in FIG. 18.

FIG. 18A shows the fluorescent labeled results obtained by incubating with the KS24 fluorescent probe for 10 min. FIG. 18B shows the fluorescent labeled results obtained by incubating with the KS24 fluorescent probe for 20 min. FIG. 18C shows the fluorescent labeled results obtained by incubating with the KS24 fluorescent probe for 40 min. FIG. 18D shows the fluorescent labeled results obtained by incubating with the KS24 fluorescent probe for 80 min. Nucblue was further used for nuclear staining. In each of FIGS. 18A, 18B, 18C, and 18D, i) is an image labeled with the KS24 fluorescent probe (shown in red in the original fluorescence color image), and ii) is an image obtained by nuclear staining with Nucblue (shown in blue in the original fluorescence color image), and iii) is a merged image of i) and ii).

Figure 18:
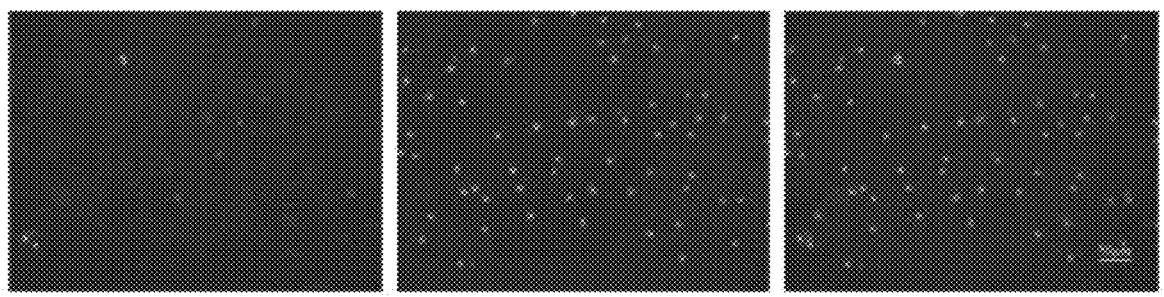
FIG. 18 shows the fluorescent labeled image obtained by staining mouse primary monocyte precursors with KS24 fluorescent probe at different incubation times.
Figure 18:
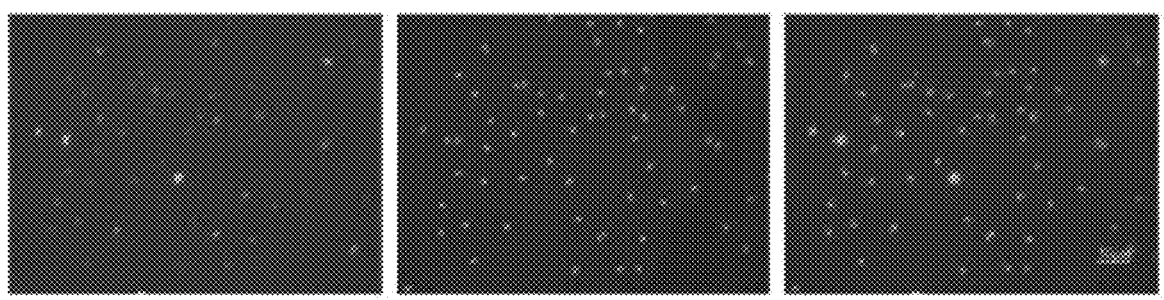
Figure 18:
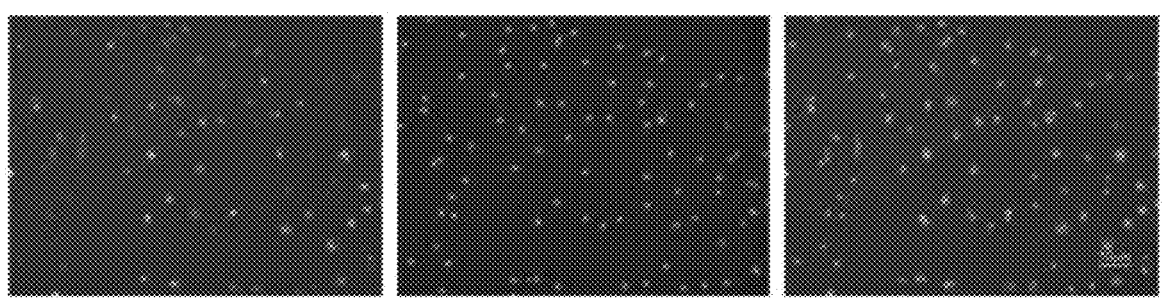
Figure 18:
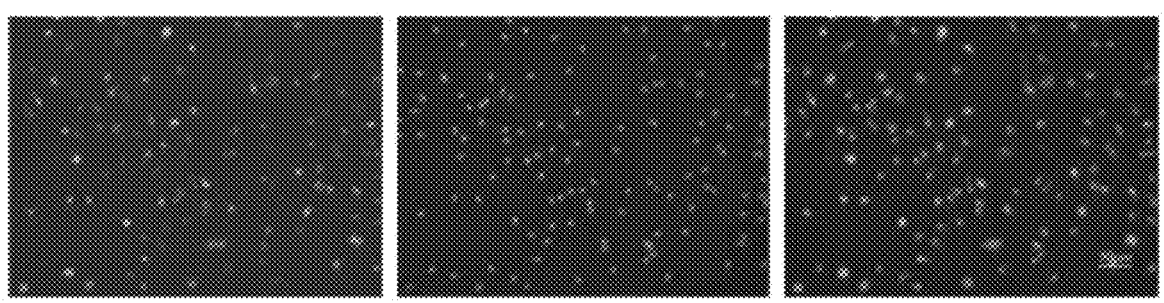

It can be seen from FIG. 18 that the KS24-labeled fluorescence of the cells gradually becomes stronger with the incubation time. The fluorescence can be even detected with microscope when incubating only for 10 min. It is sufficient to show that KS24 fluorescent probe can quickly and efficiently label monocyte precursors of mouse.

Example 21 In Vivo Fluorescent Labeling of Macrophages on Mouse Abdominal Wall by EK24 Fluorescent Probe and CD68 Antibody Referring to Example 4, using the same drug injection process, inject EK24, and FITC anti-mouse CD68 antibody (Biolegend) which was diluted with PBS from 2 μL to 500 μL. Remove mouse abdominal wall muscle for Nucblue double-staining and then observing under a fluorescence microscope (20×, light source 50%, exposure 200 ms, gain 5). The results are shown in FIG. 19.

FIG. 19A is a labeled image obtained by labeling with EK24 fluorescent probe (shown in red in the original fluorescent color image), FIG. 19B is an CD68 antibody labeled image (shown in green in the original fluorescent color image), FIG. 19C is an image obtained by nuclear staining with Nucblue (shown in blue in the original fluorescent color image), and FIG. 19D is a merged image of FIGS. 19A, 19B and 19C.

Figure 19:
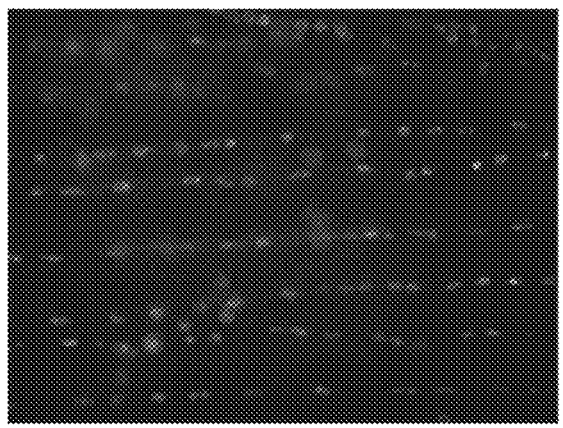
FIG. 19 shows fluorescent labeled images obtained by staining mouse abdominal wall muscle cells with the EK24 fluorescent probe and FITC anti-mouse CD68 antibody (Biolegend).
Figure 19:
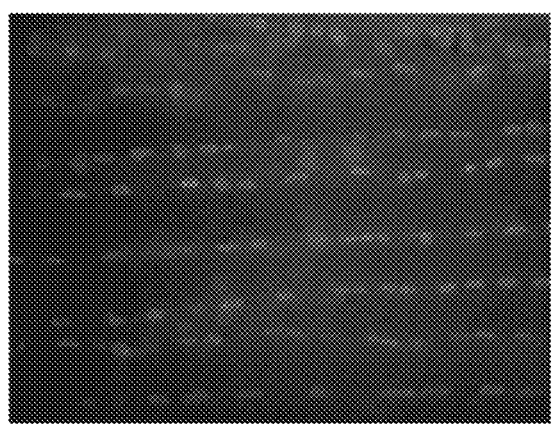
Figure 19:
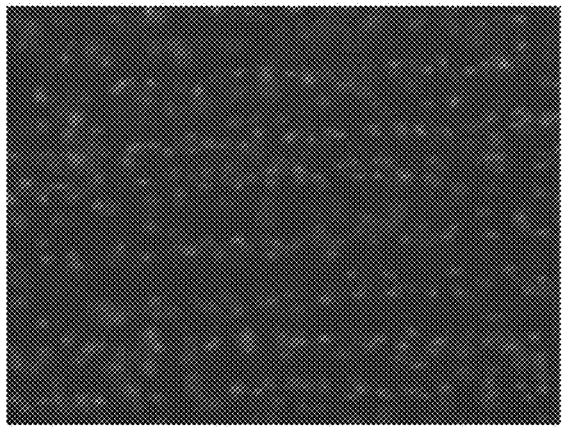
Figure 19:
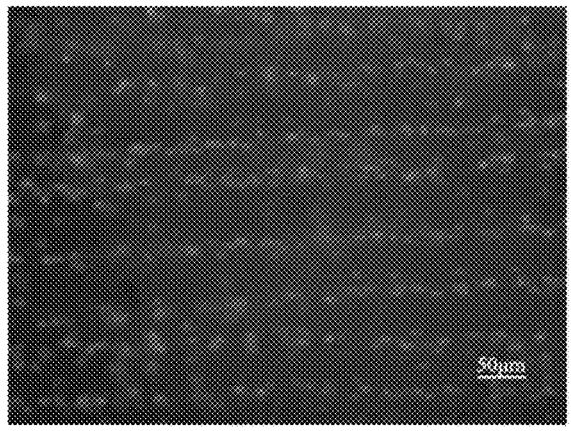

It can be seen from FIG. 19 that the macrophages on mouse abdominal wall can be labeled with the EK24 fluorescent probe, while other cells cannot be labeled.

It can be concluded from the above embodiments that the probe derived from the C-terminal fragmentses of Triokinases/FMN cyclases of human and non-human animals can effectively recognize monocyte precursors and monocytes/macrophages.

The invention claimed is:

1. A method for in vivo or in vitro imaging immune cells, comprising incubating an effective amount of a composition with cells or tissues to be labeled,
   wherein the composition comprises a polypeptide for targeting recognition of immune cells,
   wherein the polypeptide is selected from the group consisting of EQPDPGAVAAAAILRAILE (SEQ ID NO.: 1), LEQPDPGAVAAAAILRAILE (SEQ ID NO.:2), EQPDPGAVAAAAILRAILEVLQS (SEQ ID NO.:3), KNMEAGAGRASYISSARLEQPDPGAVAAAAIL-RAIL (SEQ ID NO.:4), TKNMEAGAGRASYISSAR-LEQPDPGAVAAAAILRAILEVLQS (SEQ ID NO.:5), LQPDPGAVAAAAVLRAVLEGLQG (SEQ ID NO.: 6), DQPDPGAVAAAAIFRAILEVLQTKAA (SEQ ID NO.:7), DQPDPGAVAAAAILRTILEVLQSQGV (SEQ ID NO.:8), DQPDPGAVAAAAILRAI-LEVLQSQGA (SEQ ID NO.:9) and EQPDP-GAVAAAAILRAILEVLQS (SEQ ID NO.:10),
   wherein a X or Y is linked to the C-terminal and/or N-terminal of the polypeptide; and
   wherein the X or Y is a reporter, a cysteine amino acid linked reporter or a lysine amino acid linked reporter.

2. The method according to claim 1, wherein the immune cells comprise lymphocytes, dendritic cells, monocyte precursors, monocytes, macrophages, basophilic granulocytes, eosinophilic granulocytes, and mastocytes.

3. The method according to claim 1, wherein the polypeptide for targeting recognition of immune cells is selected from the polypeptide EQPDPGAVAAAAILRAILE (SEQ ID NO.:1), LEQPDPGAVAAAAILRAILE (SEQ ID NO.:2), EQPDPGAVAAAAILRAILEVLQS (SEQ ID NO.:3) or TKNMEAGAGRASYISSARLEQPDPGAVAAAAILRAILEVLQS (SEQ ID NO.:5).

4. The method according to claim 1, wherein the polypeptide for targeting recognition of immune cells is selected from the polypeptide LQPDPGAVAAAAVLRAVLEGLQG (SEQ ID NO.:6), DQPDPGAVAAAAIFRAILEVLQTKAA (SEQ ID NO.:7), DQPDPGAVAAAAILRTILEVLQSQGV (SEQ ID NO.:8), DQPDPGAVAAAAILRAILEVLQSQGA (SEQ ID NO.:9) or EQPDPGAVAAAAILRAILEVLQS (SEQ ID NO.:10).

\* \* \* \* \*